US008877909B2

(12) United States Patent
Slater et al.

(10) Patent No.: US 8,877,909 B2
(45) Date of Patent: Nov. 4, 2014

(54) **OPTIMIZED OLIGONUCLEOTIDES AND METHODS OF USING SAME FOR THE DETECTION, ISOLATION, AMPLIFICATION, QUANTITATION, MONITORING, SCREENING, AND SEQUENCING OF GROUP B *STREPTOCOCCUS***

(75) Inventors: Damien Slater, Roslindale, MA (US); Chesley Leslin, Boston, MA (US); Juan Anzola, Bogota (CO); David Dolinger, Medway, MA (US); Alice A. Jacobs, Cambridge, MA (US)

(73) Assignee: Intelligent Medical Devices, Inc., Cambridge, MA (US)

( * ) Notice: Subject to any disclaimer, the term of this patent is extended or adjusted under 35 U.S.C. 154(b) by 0 days.

(21) Appl. No.: 13/424,022

(22) Filed: Mar. 19, 2012

(65) Prior Publication Data
US 2012/0252016 A1 Oct. 4, 2012

Related U.S. Application Data

(60) Provisional application No. 61/471,467, filed on Apr. 4, 2011.

(51) Int. Cl.
*C07H 21/02* (2006.01)
*C07H 21/04* (2006.01)
*C12Q 1/68* (2006.01)
*C12P 19/34* (2006.01)

(52) U.S. Cl.
CPC .......... *C12Q 1/689* (2013.01); *C12Q 2600/158* (2013.01)
USPC .......................... 536/23.1; 536/24.3; 435/91.2

(58) Field of Classification Search
CPC ...... C12Q 1/701; C12Q 1/689; C12Q 1/6813; C12Q 1/686; C07H 21/04
See application file for complete search history.

(56) References Cited

U.S. PATENT DOCUMENTS

| 5,620,847 | A | 4/1997 | Greisen et al. |
| 5,654,418 | A | 8/1997 | Sheiness et al. |
| 6,004,754 | A | 12/1999 | You |
| 6,054,269 | A | 4/2000 | Garnier et al. |
| 6,593,093 | B1 | 7/2003 | Uhl et al. |
| 7,141,418 | B2 | 11/2006 | Kunsch et al. |
| 7,294,466 | B2 | 11/2007 | McMillan |
| 7,438,912 | B2 | 10/2008 | Meinke et al. |
| 7,588,773 | B2 | 9/2009 | Brady et al. |
| 7,601,822 | B2 | 10/2009 | Drancourt et al. |
| 7,662,562 | B2 | 2/2010 | Hellyer et al. |
| 7,718,402 | B2 | 5/2010 | Gayral et al. |
| 7,740,870 | B2 | 6/2010 | Martin et al. |
| 7,785,780 | B2 | 8/2010 | Gala et al. |
| 7,790,412 | B2 | 9/2010 | Doucette-Stamm et al. |
| 7,790,875 | B2 | 9/2010 | Uhl et al. |
| 7,834,166 | B2 | 11/2010 | Doucette-Stamm et al. |
| 7,892,552 | B2 | 2/2011 | Adderson et al. |
| 2006/0160121 | A1 | 7/2006 | Mounter et al. |
| 2010/0028884 | A1 | 2/2010 | Gygax et al. |

FOREIGN PATENT DOCUMENTS

| EP | 1 770 171 | 4/2007 |
| WO | WO 9820157 | 5/1998 |
| WO | WO 02/092818 | 11/2002 |
| WO | WO-2009/135158 | 11/2009 |

OTHER PUBLICATIONS

Kong F. et al Journal of Medical Microbiology (2005), 54, 1133-1138.*
Haft R.F. et al. Mol Microbiol (1996) 19(3) 555-563.*
GenBank Locus SAU19899 (Mar. 25, 1997) from http://www.ncbi.nlm.nih.gov/nuccore/u19899, pp. 1-2.*
Vaya, I. et al. J. Am. Chem. Soc. 2010, 132, 11834-11835.*
Maruyama T. et al. Biotechnology Letters (2005) 27: 1349-1354.*
Bryan, J.D. et al., "Streptococcus agalactiae CspA is a serine protease that inactivates chemokines." J. Bacteriol., 2009, vol. 191, No. 6, pp. 1847-1854.
Clancy, J et al., "Cloning and Characterization of a Novel Macrolide Gene, *mreA*, from *Streptococcus agalactiae*," Antimicrobial Agents and Chemotherapy, 1997, vol. 41, No. 12, pp. 2719-2723.
Clarebout, G et al., "Macrolide Resistance Gene *mreA* of *Streptococcus agalactiae* encodes a flavokinase," Anitmicrobial Agents and Chemotherapy., 2001, vol. 45, No. 8, pp. 2280-2286.
Cvitkovitch, D.G. et al.. "Regulation of Sugar Transport via the Multiple Sugar Metabolism Operon of *Streptoccocus mutans* by the Phosphoenolpyruvate Phosphotransferase System," J. Bacteriol., 1995, vol. 177, No. 19; pp. 5704-5706.
Doran, K.S. et al., "Group B Streptococcal β-Hemolysin/Cytolysin Promotes Invasion of Human Lung Epithelial Cells and the Release of Interleukin-8," J. Infect. Dis, 2002, vol. 185, pp. 196-203.
Harris, T.O. et al., "A Novel Streptococcal Surface Protease Promotes Virulence, Resistance to Opsonophagocytosis, and Cleavage of Human Fibrinogen," J. Clin. Invest., 2003, vol. 111, No. 1; pp. 61-70.
Henneke, P et al., "Interaction of Neonatal Phagocytes with Group B *Streptococcus*: Recognition and Response," Infect. Immun., 2006, vol. 74, No. 6; pp. 3085-3095.
Kong, F. et al., "Using *cpsA-cpsB* Sequence Polymorphisms and Serotype-/Group-specific PCR to Predict 51 *Streptococcus pneumonia* capsular serotypes," J. Med. Microbiol, 2003, vol. 52, pp. 1047-1058.
Lewis, A.L. et al., "Discovery and Characterization of Sialic Acid O-Acetylation in Group B *Streptococcus*," PNAS, 2004, vol. 101, No. 30; pp. 11123-11128.
Lin, B et al., "Cloning and Expression of the Gene for Group B Streptococcal Hyaluronate Lyase," J. Biol. Chem., 1994, vol. 269, No. 48; pp. 30113-30116.
Pritzlaff, C.A. et al., Genetic Basis for the β-haemolytic/cytolytic Activity of Group B *Streptococcus*, 2001, vol. 39, No. 2; pp. 236-247.
Ganatra H A et al: "Neonatal Infections in the Developing World", Seminars in Perinatology, W.B. Saunders, GB, vol. 34, No. 6, Dec. 1, 2010, pp. 416-425.
International Search Report for PCT/US2012/029685 mailed Mar. 1, 2013.

* cited by examiner

*Primary Examiner* — Stephen Kapushoc
(74) *Attorney, Agent, or Firm* — Foley & Lardner LLP; Michel Morency

(57) ABSTRACT

Described herein are oligonucleotides useful for detecting, isolating, amplifying, quantitating, monitoring, screening and sequencing GBS genes and methods of using the described oligonucleotides.

12 Claims, 1 Drawing Sheet

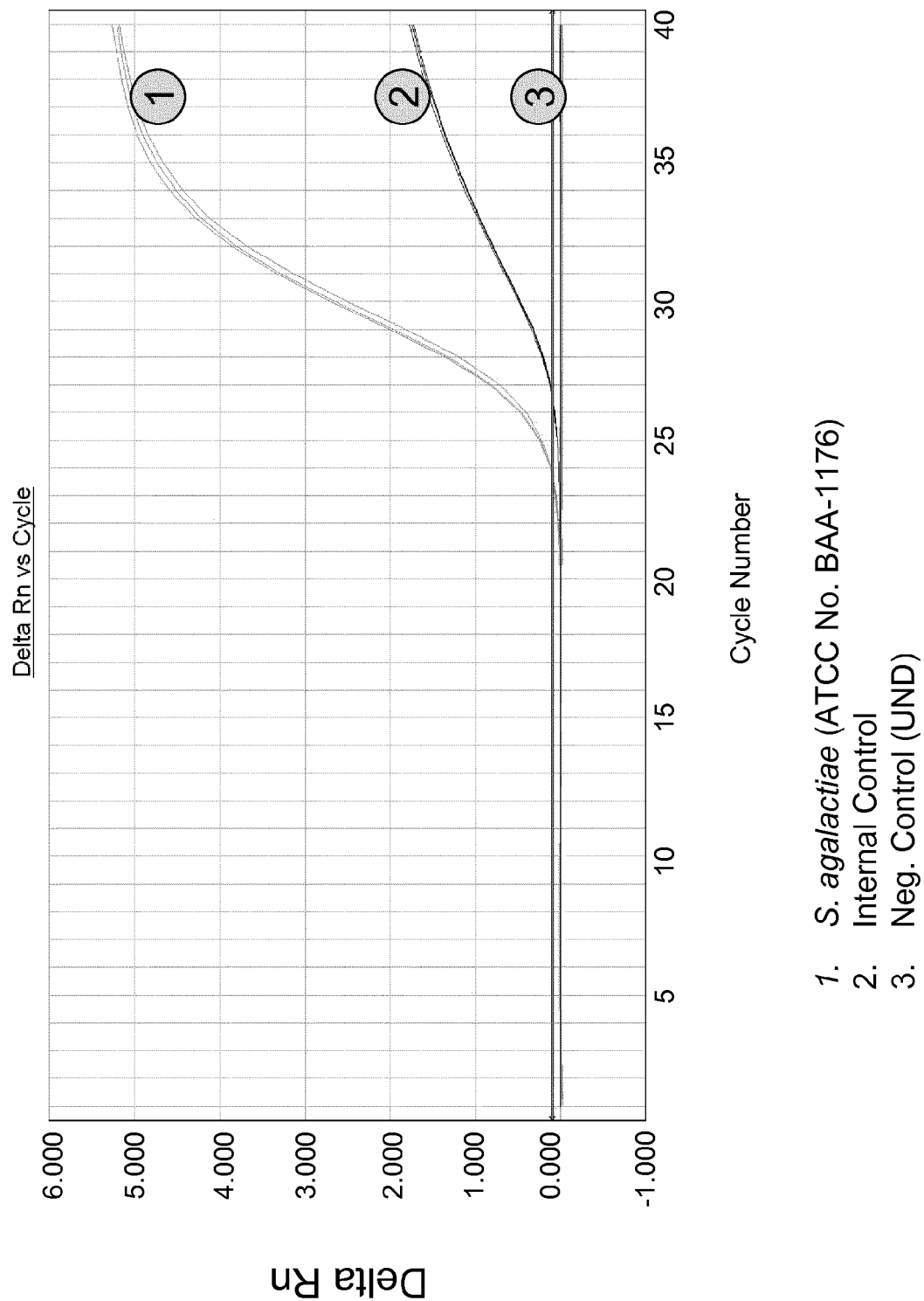

US 8,877,909 B2

OPTIMIZED OLIGONUCLEOTIDES AND METHODS OF USING SAME FOR THE DETECTION, ISOLATION, AMPLIFICATION, QUANTITATION, MONITORING, SCREENING, AND SEQUENCING OF GROUP B *STREPTOCOCCUS*

RELATED APPLICATION

This application claims the benefit of U.S. Provisional Application No. 61/471,467 filed on Apr. 4, 2011, the contents of which are incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Apr. 13, 2012, is named 09108005.txt.

FIELD OF THE INVENTION

The present invention relates to oligonucleotides for detecting, isolating, amplifying, quantitating, monitoring, screening and sequencing of Group B *Streptococcus* and methods for using the oligonucleotides.

BACKGROUND

Group B *Streptococcus* (GBS), also referred to as *Streptococcus* agalactiae, is found within the normal microflora of the gastrointestinal (GI) tract and genitourinary tract of a significant percentage of the adult human population. The bacterium can also colonize the upper respiratory tract. Although GBS are part of an individual's normal flora, the bacteria can cause septicaemia, meningitis and pneumonia amongst the elderly, immunocompromised individuals and, in particular, the neonatal population. GBS infection is the predominant cause of invasive bacterial disease in neonates.

GBS is a leading cause of early neonatal morbidity and mortality in the United States. GBS can be found in the vagina and/or rectum of 10-30% of pregnant women. Colonization status is usually determined by analysis of vaginal and rectal swabs. The CDC recommends screening for GBS at 35-37 weeks' gestation because GBS can be transmitted to neonates either before or during labor. If a woman tests positive for GBS colonization, she currently receives prophylactic antibiotic treatment. Antibiotic resistance testing may also be performed on positive samples from antenatal patients. While GBS-associated neonatal incidence has decreased substantially in recent years, GBS is still responsible for 2-3 cases of septicemia, meningitis and pneumonia per 1000 live births. Culture-based assays are currently the preferred method to detect GBS. However, obtaining results can take days, during which GBS colonization, which is transient, may occur. Therefore, a rapid and accurate screening test based on DNA to detect GBS is needed which would provide clinicians with an effective tool for identifying patients at risk of transmitting GBS to their newborns. This would in turn support effective monitoring and treatment regimens for the patients, as well as prevent overuse of antibiotics. Moreover, rapid and accurate detection of GBS infection would lead to more appropriate treatment.

SUMMARY

Described herein are oligonucleotide probes and primers for detecting, isolating, amplifying, quantitating, monitoring, screening and sequencing of Group B *Streptococcus* (GBS), specifically the neuA, cspA, cylE, hylB, mreA and ptsI genes. In one embodiment, the present invention is directed to an isolated polynucleotide, comprising a nucleotide sequence selected from the group consisting of: SEQ ID NOS: 1-35.

One embodiment is directed to a method of hybridizing one or more isolated nucleic acid sequences comprising a sequence selected from the group consisting of: SEQ ID NOS: 1-35 to a GBS sequence, comprising contacting one or more isolated nucleic acid sequences to a sample comprising the GBS sequence under conditions suitable for hybridization. In a particular embodiment, the GBS sequence is a genomic sequence, a template sequence or a sequence derived from an artificial construct. In a particular embodiment, the method(s) further comprise isolating, amplifying, quantitating, monitoring and/or sequencing the hybridized GBS sequence.

One embodiment is directed to a primer set comprising at least one forward primer selected from the group consisting of SEQ ID NOS: 1, 4, 8, 11, 14, 19, 22, 25, 30 and 33, and at least one reverse primer selected from the group consisting of SEQ ID NOS: 3, 6, 7, 10, 13, 16, 18, 21, 24, 27, 29, 32 and 35. In a particular embodiment, the primer set is selected from the group consisting of: Groups 1-13 of Table 2.

One embodiment is directed to a method of producing a nucleic acid product, comprising contacting one or more isolated nucleic acid sequences selected from the group consisting of SEQ ID NOS: 1, 3, 4, 6, 7, 8, 10, 11, 13, 14, 16, 18, 19, 21, 22, 24, 25, 27, 29, 30, 32, 33 and 35 to a sample comprising a GBS sequence under conditions suitable for nucleic acid polymerization. In a particular embodiment, the nucleic acid product is an amplicon produced using at least one forward primer selected from the group consisting of SEQ ID NOS: 1, 4, 8, 11, 14, 19, 22, 25, 30 and 33 and at least one reverse primer selected from the group consisting of SEQ ID NOS: 3, 6, 7, 10, 13, 16, 18, 21, 24, 27, 29, 32 and 35.

Particular embodiments are directed to primers and probes that hybridize to, amplify and/or detect GBS markers selected from the group consisting of: neuA, cspA, cylE, hylB, mreA and ptsI, and methods of using the primers and probes.

One embodiment is directed to a probe that hybridizes to an amplicon produced as described herein, e.g., using the primers described herein. In a particular embodiment, the probe comprises a sequence selected from the group consisting of: SEQ ID NOS: 2, 5, 9, 12, 15, 17, 20, 23, 26, 28, 31 and 34. In a particular embodiment, the probe is labeled with a detectable label selected from the group consisting of: a fluorescent label, a chemiluminescent label, a quencher, a radioactive label, biotin, mass tags and/or gold. The probe may also be labeled with other similar detectable labels used in conjunction with probe technology as known by one of ordinary skill in the art.

One embodiment is directed to a set of probes that hybridize to an amplicon produced as described herein, e.g., using the primers described herein, or that directly hybridizes to the target nucleic acid sequence. In a particular embodiment, a first probe comprises a sequence selected from the group consisting of: SEQ ID NOS: 2, 5, 9, 12, 15, 17, 23, 26, 28, 31 and 34, and a second probe comprises SEQ ID NO: 20. In a particular embodiment, the first probe is labeled with a first detectable label and the second probe is labeled with a second detectable label. In a particular embodiment, the first probe and the second probe are labeled with the same detectable label. In a particular embodiment, the detectable labels are selected from the group consisting of: a fluorescent label, a chemiluminescent label, a quencher, a radioactive label, biotin, mass tags and gold. The probe may also be labeled with other similar detectable labels used in conjunction with probe technology as known by one of ordinary skill in the art.

In one embodiment, the present invention is directed to simultaneous detection in a singleplex or multiplex format of (1) neuA; and/or (2) cspA and/or (3) cylE; and/or (4) hylB; and/or (5) mreA; and/or (6) pstI. These probes will provide identification of GBS genes that code for NeuA and/or CspA and/or CylE and/or HylB and/or MreA and/or PstI. Such an embodiment can be used in a diagnostic assay or in a screening assay.

One embodiment is directed to a method for detecting a GBS sequence in a sample, comprising: a) contacting the sample with at least one forward primer comprising a sequence selected from the group consisting of: SEQ ID NOS: 1, 4, 8, 11, 14, 19, 22, 25, 30 and 33, and at least one reverse primer comprising a sequence selected from the group consisting of: SEQ ID NOS: 3, 6, 7, 10, 13, 16, 18, 21, 24, 27, 29, 32 and 35 under conditions such that nucleic acid amplification occurs to yield an amplicon; and b) contacting the amplicon with one or more probes comprising one or more sequences selected from the group consisting of: SEQ ID NOS: 2, 5, 9, 12, 15, 17, 20, 23, 26, 28, 31 and 34 under conditions such that hybridization of the probe to the amplicon occurs, wherein hybridization of the probe is indicative of GBS in the sample. In a particular embodiment, each of the one or more probes is labeled with a different detectable label. In a particular embodiment, the one or more probes are labeled with the same detectable label. In a particular embodiment, the sample is selected from the group consisting of: blood, serum, plasma, enriched peripheral blood mononuclear cells, fecal material, urine, neoplastic or other tissue obtained from biopsies, cerebrospinal fluid, saliva, fluids collected from the ear, eye, mouth, and respiratory airways, sputum, stool, skin, gastric secretions, oropharyngeal swabs, nasopharyngeal swabs, throat swabs, rectal swabs, per-rectal swabs, vaginal swabs, nasal aspirates, nasal wash, renal tissue, and fluid therefrom including perfusion media, pure cultures of bacterial fungal isolates, fluids and cells obtained by the perfusion of tissues of both human and animal origin, and fluids and cells derived from the culturing of human cells, including human stem cells and human cartilage or fibroblasts, pure cultures of bacterial fungal isolates, and swabs or washes of environmental surfaces, or other samples derived from environmental surfaces. In a particular embodiment, the sample is from a human, is non-human in origin, or is derived from an inanimate object.

In a particular embodiment, the at least one forward primer, the at least one reverse primer and the one or more probes are selected from the group consisting of: Groups 1-13 of Table 2. In a particular embodiment, the method(s) further comprise quantitating and/or sequencing GBS sequences in a sample.

One embodiment is directed to a method for detecting a GBS sequence in a sample, comprising one or more probes comprising a sequence selected from the group consisting of: SEQ ID NOS: 2, 5, 9, 12, 15, 17, 20, 23, 26, 28, 31 and 34 under conditions such that hybridization of the probe to the GBS sequence occurs, wherein hybridization of the probe is indicative of GBS in the sample. In a particular embodiment, the method(s) further comprise quantitating and/or sequencing GBS sequences in a sample.

One embodiment is directed to a primer set or collection of primer sets for amplifying sequences from GBS, including the marker genes neuA, cspA, cylE, hylB, mreA and ptsI, comprising a nucleotide sequence selected from the group consisting of: a primer set selected from the group consisting of: (1) SEQ ID NOS: 1 and 3; (2) SEQ ID NOS: 4 and 6; (3) SEQ ID NOS: 4 and 7; (4) SEQ ID NOS: 8 and 10; (5) SEQ ID NOS: 11 and 13; (6) SEQ ID NOS: 14 and 16; (7) SEQ ID NOS: 14 and 18; (8) SEQ ID NOS: 19 and 21; (9) SEQ ID NOS: 22 and 24; (10) SEQ ID NOS: 25 and 27; (11) SEQ ID NOS: 22 and 29; (12) SEQ ID NOS: 30 and 32; and (13) SEQ ID NOS: 33 and 35. A particular embodiment is directed to oligonucleotide probes for binding to the GBS sequences encoding NeuA, CspA, CylE, HylB, MreA and PtsI markers comprising a nucleotide sequence selected from the group consisting of: SEQ ID NOS: 2, 5, 9, 12, 15, 17, 20, 23, 26, 28, 31 and 34.

One embodiment is directed to a primer set for amplifying sequences from a GBS neuA gene, comprising SEQ ID NOS: 1 and 3. A particular embodiment is directed to an oligonucleotide probe for binding to the GBS neuA gene, comprising SEQ ID NO: 2.

One embodiment is directed to a primer set for amplifying sequences from a GBS cspA gene, comprising a nucleotide sequence selected from the group consisting of: (1) SEQ ID NOS: 4 and 6; (2) SEQ ID NOS: 4 and 7; and (3) SEQ ID NOS: 8 and 10. A particular embodiment is directed to oligonucleotide probes for binding to sequences encoding the GBS cspA gene, comprising a nucleotide sequence selected from the group consisting of: SEQ ID NOS: 5 and 9.

One embodiment is directed to a primer set for amplifying sequences from a GBS cylE gene, comprising SEQ ID NOS: 11 and 13. A particular embodiment is directed to an oligonucleotide probe for binding to the GBS cylE gene, comprising SEQ ID NO: 12.

One embodiment is directed to a primer set for amplifying sequences from a GBS hylB gene, comprising a nucleotide sequence selected from the group consisting of: (1) SEQ ID NOS: 14 and 16; and (2) SEQ ID NOS: 14 and 18. A particular embodiment is directed to oligonucleotide probes for binding to the GBS hylB gene, comprising a nucleotide sequence selected from the group consisting of: SEQ ID NOS: 15 and 17.

One embodiment is directed to a primer set for amplifying sequences from a GBS mreA gene, comprising SEQ ID NOS: 19 and 21. A particular embodiment is directed to an oligonucleotide probe for binding to the GBS mreA gene, comprising SEQ ID NO: 20.

One embodiment is directed to a primer set for amplifying sequences from a GBS ptsI gene, comprising a nucleotide sequence selected from the group consisting of: (1) SEQ ID NOS: 22 and 24; (2) SEQ ID NOS: 25 and 27; (3) SEQ ID NOS: 22 and 29; (4) SEQ ID NOS: 30 and 32; and (5) SEQ ID NOS: 33 and 35. A particular embodiment is directed to oligonucleotide probes for binding to the GBS ptsI gene, comprising a nucleotide sequence selected from the group consisting of: SEQ ID NOS: 23, 26, 28, 31 and 34.

One embodiment is directed to a kit for detecting GBS sequences in a sample, comprising one or more probes comprising a sequence selected from the group consisting of: SEQ ID NOS: 2, 5, 9, 12, 15, 17, 20, 23, 26, 28, 31 and 34. In a particular embodiment, the kit further comprises a) at least one forward primer comprising the sequence selected from the group consisting of: SEQ ID NOS: 1, 4, 8, 11, 14, 19, 22, 25, 30 and 33; and b) at least one reverse primer comprising the sequence selected from the group consisting of: SEQ ID NOS: 3, 6, 7, 10, 13, 16, 18, 21, 24, 27, 29, 32 and 35. In a particular embodiment, the kit further comprises reagents for quantitating and/or sequencing GBS sequences in the sample. In a particular embodiment, the one or more probes are labeled with different detectable labels. In a particular embodiment, the one or more probes are labeled with the same detectable label. In a particular embodiment, the at least one forward primer and the at least one reverse primer are selected from the group consisting of: Groups 1-13 of Table 2.

One embodiment is directed to a method of diagnosing a GBS-associated complication, condition, syndrome or disease, comprising: a) contacting a sample with at least one forward and reverse primer set selected from the group consisting of: Groups 1-13 of Table 2; b) conducting an amplification reaction, thereby producing an amplicon; and c) detecting the amplicon using one or more probes selected from the group consisting of: SEQ ID NOS: 2, 5, 9, 12, 15, 17, 20, 23, 26, 28, 31 and 34; wherein the detection of an amplicon is indicative of the presence of GBS in the sample. In a particular embodiment, the sample is selected from the group consisting of: blood, serum, plasma, enriched peripheral blood mononuclear cells, fecal material, urine, neoplastic or other tissue obtained from biopsies, cerebrospinal fluid, saliva, fluids collected from the ear, eye, mouth, and respiratory airways, sputum, stool, skin, gastric secretions, oropharyngeal swabs, nasopharyngeal swabs, throat swabs, peri-rectal swabs, rectal swabs, vaginal swabs, nasal aspirates, nasal wash, renal tissue, and fluid therefrom including perfusion media, pure cultures of bacterial fungal isolates, fluids and cells obtained by the perfusion of tissues of both human and animal origin, and fluids and cells derived from the culturing of human cells, including human stem cells and human cartilage or fibroblasts, pure cultures of bacterial fungal isolates, and swabs or washes of environmental surfaces, or other samples derived from environmental surfaces. In a particular embodiment, the sample is from a human, is non-human in origin, or is derived from an inanimate object. In a particular embodiment, the GBS-associated complication, condition, syndrome or disease is selected from the group consisting of: urinary tract infection, meningitis, pneumonia, chorioamnionitis, endometritis, endocarditis, skin infections, such as boils, impetigo, cellulitis, and scalded skin syndrome; bacteremia, resulting in a persistent fever and other signs of blood poisoning; fever, nausea, vomiting, rash on palms and soles, confusion, muscle aches, seizures, headache; bone and joint infections; septic arthritis, resulting in joint swelling, severe pain in the affected joint, fever and shaking chills; early onset disease in infants, resulting in fever, difficulty and lethargy and late-onset disease in infants, resulting in coughing, congestion, fever, difficulty feeding, lethargy and seizures.

One embodiment is directed to a kit for amplifying and sequencing GBS sequences in a sample, comprising: a) at least one forward primer comprising the sequence selected from the group consisting of: SEQ ID NOS: 1, 4, 8, 11, 14, 19, 22, 25, 30 and 33; b) at least one reverse primer comprising the sequence selected from the group consisting of: SEQ ID NOS: 3, 6, 7, 10, 13, 16, 18, 21, 24, 27, 29, 32 and 35; c) reagents for the sequencing of amplified DNA fragments; and d) an internal control, positive control or a process control. In a particular embodiment, the kit further comprises reagents for quantitating GBS marker sequences in the sample.

One embodiment is directed to a method of diagnosing a GBS-associated complication, condition, syndrome or disease, comprising contacting a denatured target from a sample with one or more probes comprising a sequence selected from the group consisting of: SEQ ID NOS: 2, 6, 9, 12, 14, 17, 20, 23, 25, 28, 31 and 34 under conditions for hybridization to occur; wherein hybridization of the one or more probes to a denatured target is indicative of the presence of GBS in the sample. In a particular embodiment, the sample is selected from the group consisting of: blood, serum, plasma, enriched peripheral blood mononuclear cells, fecal material, urine, neoplastic or other tissue obtained from biopsies, cerebrospinal fluid, saliva, fluids collected from the ear, eye, mouth, and respiratory airways, sputum, stool, skin, gastric secretions, oropharyngeal swabs, nasopharyngeal swabs, throat swabs, peri-rectal swabs, rectal swabs, vaginal swabs, nasal aspirates, nasal wash, renal tissue, and fluid therefrom including perfusion media, pure cultures of bacterial fungal isolates, fluids and cells obtained by the perfusion of tissues of both human and animal origin, and fluids and cells derived from the culturing of human cells, including human stem cells and human cartilage or fibroblasts, pure cultures of bacterial fungal isolates, and swabs or washes of environmental surfaces, or other samples derived from environmental surfaces. In a particular embodiment, the sample is from a human, is non-human in origin, or is derived from an inanimate object. In a particular embodiment, the GBS-associated complication, condition, syndrome or disease is selected from the group consisting of: urinary tract infection, meningitis, pneumonia, chorioamnionitis, endometritis, endocarditis, skin infections, such as boils, impetigo, cellulitis, and scalded skin syndrome; bacteremia, resulting in a persistent fever and other signs of blood poisoning; fever, nausea, vomiting, rash on palms and soles, confusion, muscle aches, seizures, headache; bone and joint infections; septic arthritis, resulting in joint swelling, severe pain in the affected joint, fever and shaking chills; early onset disease in infants, resulting in fever, difficulty and lethargy and late-onset disease in infants, resulting in coughing, congestion, fever, difficulty feeding, lethargy and seizures.

One embodiment is directed to screening and/or a screening kit for detecting and/or amplifying and/or sequencing GBS sequences comprising one or more probes comprising one or more sequences selected from the group consisting of: SEQ ID NOS: 2, 5, 9, 12, 15, 17, 20, 23, 26, 28, 31 and 34. In a particular embodiment, the kit further comprises a) at least one forward primer comprising the sequence selected from the group consisting of: SEQ ID NOS: 1, 4, 8, 11, 14, 19, 22, 25, 30 and 33; and b) at least one reverse primer comprising the sequence selected from the group consisting of: SEQ ID NOS: 3, 6, 7, 10, 13, 16, 18, 21, 24, 27, 29, 32 and 35. In a particular embodiment, the kit further comprises reagents for quantitating GBS sequences in the sample. In a particular embodiment, the kit further comprises a process control and/or a positive control and/or a negative control. A process control is added directly to the reaction mix to monitor the integrity of the PCR reagents and the presence of PCR inhibitors. A negative control is added to ensure that the primers and probes are not binding nonspecifically. The target may be acquired from, for example, antepartum and/or intrapartum women.

Another embodiment of the invention is directed to a process control. Bacterial material from a gram-positive bacterium, *Geobacillus stearothermophilus*, not related to GBS, is incorporated into a kit as a separate component. The process control bacterial material will be cultured and aliquoted at a known titer. These aliquots will be provided as nucleic acid extraction controls. Known amounts of the process control bacterial material will be spiked into a test sample by the user of the test kit. Nucleic acids will be extracted from the test sample and subjected to PCR to detect GBS and *Geobacillus*-specific target genes. The *Geobacillus*-specific target genes are disclosed in Table 5. Primers and probes described in Table 4 will be used to amplify and detect the *Geobacillus* gene(s). Detection of the *Geobacillus* gene(s) indicates that nucleic acid extraction from the test sample was successful.

A GBS positive control plasmid contains partial sequences for one or more of the GBS markers (i.e., neuA and/or cspA and/or cylE and/or hylB and/or mreA and/or ptsI). An example of a positive control partial sequence is provided in Table 3. The positive control plasmid comprises forward primer, probe and reverse primer sequences for the given GBS markers. An artificial polynucleotide sequence is inserted within the positive control sequence corresponding to the given target to allow the amplicon generated by the target primer pairs to be differentiated from the amplicon derived by the same primer pairs from a natural target by size, by a unique restriction digest profile, and by a probe directed against the artificial sequence. The positive control plasmids are intended to be used as a control to confirm that the assay is performing within specifications.

The negative control will comprise purified genomic DNA from an unrelated bacterium, *Bacteroides thetaiotaomicron*. The negative control is necessary to test for nonspecific binding of the primers and probes of the invention.

BRIEF DESCRIPTION OF THE DRAWINGS

FIG. 1 depicts an amplification plot corresponding to Ct values listed in Table 6.

DETAILED DESCRIPTION

Although GBS is a normal part of an individual's microflora, the bacterium can cause significant invasive disease in immunocompromised individuals, including elderly persons and neonates. Studies have shown an increase in frequency of GBS infections, usually presented as bacteremia, among elderly and diabetic patients in recent years. GBS is the predominant cause of invasive bacterial disease in the neonate. GBS can cause infection within the first week of life (early-onset disease), as well as up to six months of life (late-onset disease), before the infant develops an adequate immune response. In early-onset disease, infection primarily occurs by GBS colonization of the neonate before or during birth. Pregnant women colonized with GBS were found to be much more likely to give birth to children with early-onset disease than pregnant women testing negative for GBS. The exact mechanism of colonization is unclear. But, studies have shown that GBS can ascend up the vaginal tract through the amniotic membrane and/or colonize the amniotic fluid upon rupture of the membrane after onset of labor. GBS may be aspirated subsequently into the neonate's lungs and from there can enter the bloodstream. (Centers for Disease Control and Prevention. Prevention of Perinatal Group B Streptococcal Disease. MMWR 59(No. RR:10):1-33 (2010)). The contents of all references are incorporated herein in their entirety.

Pregnant women may be treated prophylactically with intravenous antibiotics, namely beta-lactam antibiotics, such as penicillin and ampicillin. Alternative therapies include erythromycin and clindamycin for those sensitive to the beta-lactam antibiotics. This preventive treatment has reduced significantly the burden of early-onset disease. However, widespread use has created concern about the emergence of antibiotic-resistant GBS. This concern, along with safety concerns (e.g., allergies to antibiotics), necessitates proper screening of candidates for antibiotic treatment both before and during labor.

The CDC recommends that pregnant women are tested for GBS at 35 to 37 weeks' gestation. Specimen collection usually involves a swab test of the pregnant woman's vagina and rectum. These samples undergo selective broth enrichment. The enriched samples are plated on selective media plates and incubated for 24-48 hours. The bacteria form gray-white colonies surrounded by a zone of beta hemolysis on sheep blood agar. Culture-based screening has been widely used to identify candidates for antibiotic treatment. The CDC recommends that women testing positive for GBS at 35 to 37 weeks' gestation undergo prophylactic treatment to eradicate the GBS and reduce the likelihood of GBS transmission to the neonate. (Centers for Disease Control and Prevention. Prevention of Perinatal Group B Streptococcal Disease. MMWR 59(No. RR:10):1-33 (2010))

GBS colonization of the vagina and/or rectum is transient. Consequently, one who tests positive at 35-37 weeks' gestation (antepartum) may not have GBS at the time of labor. Therefore, if a rapid screening assay (2 hours or less) was used at the time of delivery, and the patient tested negative, a clinician would not need to administer antibiotics, reducing the risks associated with antibiotics and their overuse. If the patient tested positive intrapartum, the clinican could administer antibiotics at that time. More rapid and frequent screening of GBS pathogens can lead to more time-appropriate and effective treatment of a subject.

GBS produces numerous virulence factors that contribute to its pathogenesis. A polysaccharide capsule helps the bacterium to evade the innate immune response by inhibiting opsonization and subsequent phagocytosis by immune cells. However, GBS also contains other virulence factors and marker genes that can be used for species identification.

NeuA is a protein involved in biogenesis of the cell wall. This protein modulates O-acetylation of the GBS sialic-acid capped capsular polysaccharide. Modulation of this capsule mediates evasion of complement-mediated killing by the innate immune response (Lewis et al., Proc Nat. Acad. Sci., 101(3):11123-11128 (2004)).

The cspA gene encodes a cell surface associated protease that plays an important role in GBS pathogenesis. This surface protein is required for GBS cleavage of human fibrinogen. Mutants lacking CspA exhibited a significant decrease in infectivity in a neonatal rat model. (Harris et al. *J. Clin. Invest*, 111:61-70 (2003)). Recent studies have suggested that CspA inactivates chemokines that are important in the activation and chemotaxis of neutrophils. (Bryan et al. *J. Bacteriol*, 191(6):1847-1854 (2009)).

CylE encodes the pore-forming membrane toxin B-hemolysin that contributes to its pathogenesis. This protein has hemolytic and cytolytic activity against a broad range of host cells. CylE has also been shown to facilitate invasion of human lung epithelial cells as well as promoting host cell release of interleukin-8, a neutrophil chemoattractant. (Doran et al. *J. Infect Dis.*, 185:196-203 (2002)).

The hylB gene encodes hyaluronate lyase, a secreted protein that degrades hyaluronic acid, an important extracellular matrix protein. This degradation plays a role in intercellular spread of the organism and exposes host cells more readily to bacterial toxins. (Lin et al., J. Biol. Chem., 269(48):30113-30116 (1994)).

MreA confers macrolide resistance to GBS. Certain strains of GBS have been shown to be resistant to macrolides and clindamycin by active efflux of the antibiotic. MreA shares significant homology with flavokinases and exhibits flavokinase activity. Flavokinases convert riboflavin to flavin mononucleotide (FMN). MreA may play a role in a novel type of macrolide efflux mechanism. (Clarebout et al., Antimicrob. Agents Chemo. 45(8):2280-2286 (2001)).

PtsI is a phosphoenolpyruvate-protein phosphotransferase. This protein is a component of the phosphoenolpyruvate: sugar phostphotransferase system that catalyzes sugar transport and controls metabolism in response to carbohydrate availability. (Cvitkovitch et al., J. Bacteriol., 177(19):5704-5706 (1995)).

Described herein are optimized oligonucleotides that can act as probes and primers that, alone or in various combinations, allow for the detection, isolation, amplification, quantitation, monitoring, screening and sequencing of GBS pathogens. Screening refers to a test or exam performed on a patient to find a condition before symptoms begin. Monitoring generally means to be aware of the state of a system. Oligonucleotide primers and probes for detecting bacterial or derived genetic material of GBS and methods for designing and optimizing the respective primer and probe sequences are described. Optimized primer and probe sets were designed to target genes that are either conserved within the GBS genome or acquired readily by GBS (e.g., antibiotic resistance genes).

The primers and probes described herein can be used, for example, to confirm suspected cases of GBS-associated diseases, symptoms, disorders or conditions, e.g., septicaemia or pneumonia and to determine if the causative agent is GBS in a singleplex format.

The primers and probes described herein can also be used, for example, to confirm suspected cases of GBS-associated diseases, symptoms, disorders or conditions, e.g., septicaemia or pneumonia and to determine if the causative agent is GBS and/or antibiotic resistant GBS in a multiplex format. The multiplex format option allows relative comparisons to be made between these genes. For example, a multiplex assay could detect both the antibiotic resistance gene, mreA, and the neuA gene to determine if co-infection with both GBS and an antibiotic resistant strain of GBS has occurred.

In another embodiment, these oligonucleotides may be used as part of a screening kit for detecting GBS within a sample acquired from, for example, an antepartum or intrapartum women. The individual from whom the sample is acquired may or may not be symptomatic; thus a positive result from a screen would permit the hospital or doctor to perform the appropriate preventative measures to avoid transmission of GBS to the newborn infant(s).

The primers and probes of the present invention can be used for the detection of GBS containing the genes neuA and/or cspA and/or cylE and/or hylB and/or mreA and/or ptsI without loss of assay precision or sensitivity. Furthermore, the primers and probes of the present invention can be combined with the process control and/or positive control and/or negative control without a loss of assay sensitivity.

GBS-associated colonization, complications, conditions, syndromes or diseases in mammals, e.g., humans, include, but are not limited to: urinary tract infection, meningitis, pneumonia, chorioamnionitis, endometritis, endocarditis, skin infections, such as boils, impetigo, cellulitis, and scalded skin syndrome; bacteremia, resulting in a persistent fever and other signs of blood poisoning; fever, nausea, vomiting, rash on palms and soles, confusion, muscle aches, seizures, headache; bone and joint infections; septic arthritis, resulting in joint swelling, severe pain in the affected joint, fever and shaking chills; early onset disease in infants, resulting in fever, difficulty and lethargy and late-onset disease in infants, resulting in coughing, congestion, fever, difficulty feeding, lethargy and seizures.

Detection and/or screening of GBS pathogens can lead to earlier and more effective treatment of a subject. The methods for detecting GBS colonization described herein can be coupled with effective treatment therapies. The B-lactam antibiotics comprising penicillin and ampicillin are often prescribed for treatment of a GBS infection. For those sensitive to B-lactam antibiotics, erythromycin and clindamycin are frequently prescribed.

There is a particular need for a screening kit containing oligonucleotides that may be used for detecting GBS within a sample acquired from antepartum and intrapartum women. Accurate and frequent assessment of GBS colonization would help decrease overuse of antibiotics and, as a result, decrease the emergence of antibiotic-resistant GBS strains.

The present invention, therefore, provides a method for specifically detecting the presence of a GBS pathogen in a given sample using the primers and probes provided herein. Of particular interest in this regard is the ability of the disclosed primers and probes, as well as those that can be designed according to the disclosed methods, to specifically detect all or a majority of presently characterized strains of GBS. The optimized primers and probes are useful, therefore, for identifying and diagnosing the causative or contributing agents of disease caused by a GBS pathogen, whereupon an appropriate treatment can then be administered to the individual to eradicate the bacteria.

The present invention provides one or more sets of primers that can anneal to all currently identified strains of the GBS species and thereby amplify a target from a biological sample. The present invention provides, for example, at least a first primer and at least a second primer for GBS, each of which comprises a nucleotide sequence designed according to the inventive principles disclosed herein, which are used together to amplify DNA from GBS in a sample in a singleplex assay, or GBS in a sample in a multiplex assay, regardless of the actual nucleotide composition of the infecting bacterial strain(s).

Also provided herein are probes that hybridize to the GBS sequences and/or amplified products derived from the GBS sequences. A probe can be labeled, for example, such that when it binds to an amplified or unamplified target sequence, or after it has been cleaved after binding, a fluorescent signal is emitted that is detectable under various spectroscopy and light measuring apparatuses. The use of a labeled probe, therefore, can enhance the sensitivity of detection of a target in an amplification reaction of GBS sequences because it permits the detection of bacterial-derived DNA at low template concentrations that might not be conducive to visual detection as a gel-stained amplification product.

Primers and probes are sequences that anneal to a bacterial genomic or bacterial genomic derived sequence, e.g., GBS sequences, e.g., neuA, cspA, cylE, hylB, mreA and ptsI (the "target" sequences). The target sequence can be, for example, a bacterial genome or a subset, "region", of, in this case, a bacterial genome. In one embodiment, the entire genomic sequence can be "scanned" for optimized primers and probes useful for detecting bacterial strains. In other embodiments, particular regions of the bacterial genome can be scanned, e.g., regions that are documented in the literature as being useful for detecting multiple strains, regions that are conserved, or regions where sufficient information is available in, for example, a public database, with respect to bacterial strains.

Sets or groups of primers and probes are generated based on the target to be detected. The set of all possible primers and probes can include, for example, sequences that include the variability at every site based on the known bacterial strains, or the primers and probes can be generated based on a consensus sequence of the target. The primers and probes are generated such that the primers and probes are able to anneal to a particular strain or sequence under high stringency conditions. For example, one of ordinary skill in the art recognizes that for any particular sequence, it is possible to provide more than one oligonucleotide sequence that will anneal to the particular target sequence, even under high stringency conditions. The set of primers and probes to be sampled includes, for example, all such oligonucleotides for all bacterial strain sequences. Alternatively, the primers and probes include all such oligonucleotides for a given consensus sequence for a target.

Typically, stringent hybridization and washing conditions are used for nucleic acid molecules over about 500 bp. Stringent hybridization conditions include a solution comprising about 1 M $Na^+$ at 25° C. to 30° C. below the Tm; e.g., 5×SSPE, 0.5% SDS, at 65° C.; (see, Ausubel, et al., *Current Protocols in Molecular Biology*, Greene Publishing, 1995; Sambrook et al., *Molecular Cloning: A Laboratory Manual*, Cold Spring Harbor Press, 1989). Tm is dependent on both the G+C content and the concentration of salt ions, e.g., $Na^+$ and $K^+$ A formula to calculate the Tm of nucleic acid molecules greater than about 500 bp is $Tm=81.5+0.41(\% (G+C))-\log_{10}[Na^+]$. Washing conditions are generally performed at least at equivalent stringency conditions as the hybridization. If the background levels are high, washing can be performed at higher stringency, such as around 15° C. below the Tm.

The set of primers and probes, once determined as described above, are optimized for hybridizing to a plurality of bacterial strains by employing scoring and/or ranking steps that provide a positive or negative preference or "weight" to certain nucleotides in a target nucleic acid strain sequence. If a consensus sequence is used to generate the full set of primers and probes, for example, then a particular primer sequence is scored for its ability to anneal to the corresponding sequence of every known native strain sequence. Even if a probe were originally generated based on a consensus, therefore, the validation of the probe is in its ability to specifically anneal and detect every, or a large majority of, bacterial strain sequences. The particular scoring or ranking steps performed depend upon the intended use for the primer and/or probe, the particular target nucleic acid sequence, and the number of strains of that target nucleic acid sequence. The methods of the invention provide optimal primer and probe sequences because they hybridize to all or a subset of strains of the GBS species. Once optimized oligonucleotides are identified that can anneal to bacterial strains, the sequences can then further be optimized for use, for example, in conjunction with another optimized sequence as a "primer set" or for use as a probe. A "primer set" is defined as at least one forward primer and one reverse primer.

Described herein are methods for using the GBS primers and probes for producing a nucleic acid product, for example, comprising contacting one or more nucleic acid sequences of SEQ ID NOS: 1-35 to a sample comprising at least one of the strains of GBS under conditions suitable for nucleic acid polymerization. The primers and probes can additionally be used to quantitate and/or sequence GBS sequences, or used as a diagnostic to, for example, detect GBS in a sample, e.g., obtained from a subject, e.g., a mammalian subject. The primers and probes can additionally be used to screen for GBS in a sample. Particular combinations for amplifying GBS sequences include, for example, using at least one forward primer selected from the group consisting of SEQ ID NOS: 1, 4, 8, 11, 14, 19, 22, 25, 30 and 33 and at least one reverse primer selected from the group consisting of SEQ ID NOS: 3, 6, 7, 10, 13, 16, 18, 21, 24, 27, 29, 32 and 35.

Methods are described for detecting or screening for GBS pathogens in a sample, for example, comprising (1) contacting at least one forward and reverse primer set, e.g., SEQ ID NOS 1, 4, 8, 11, 14, 19, 22, 25, 30 and 33 (forward primers) and SEQ ID NOS: 3, 6, 7, 10, 13, 16, 18, 21, 24, 27, 29, 32 and 35 (reverse primers) to a sample; (2) conducting an amplification; and (3) detecting the generation of an amplified product, wherein the generation of an amplified product indicates the presence of GBS in the sample.

The detection of amplicons using probes described herein can be performed, for example, using a labeled probe, e.g., the probe comprising a nucleotide sequence selected from the group consisting of: SEQ ID NOS: 2, 5, 9, 12, 15, 17, 20, 23, 26, 28, 31 and 34, that hybridizes to one of the strands of the amplicon generated by at least one forward and reverse primer set. The probes can also bind directly to the target sequence. The probe(s) can be, for example, fluorescently labeled, thereby indicating that the detection of the probe involves measuring the fluorescence of the sample of the bound probe, e.g., after bound probes have been isolated. Probes can also be fluorescently labeled in such a way, for example, such that they only fluoresce upon hybridizing to their target, thereby eliminating the need to isolate hybridized probes. The probe can also comprise a fluorescent reporter moiety and a quencher of fluorescence moiety. Upon probe hybridization with the amplified product, the exonuclease activity of a DNA polymerase can be used to cleave the probe reporter and quencher, resulting in the unquenched emission of fluorescence, which is detected. An increase in the amplified product causes a proportional increase in fluorescence, due to cleavage of the probe and release of the reporter moiety of the probe. The amplified product is quantified in real time as it accumulates. For multiplex reactions involving more than one distinct probe, each of the probes can be labeled with a different distinguishable and detectable label.

The probes can be molecular beacons. Molecular beacons are single-stranded probes that form a stem-loop structure. A fluorophore can be, for example, covalently linked to one end of the stem and a quencher can be covalently linked to the other end of the stem forming a stem hybrid. When a molecular beacon hybridizes to a target nucleic acid sequence, the probe undergoes a conformational change that results in the dissociation of the stem hybrid and, thus the fluorophore and the quencher move away from each other, enabling the probe to fluoresce brightly. Molecular beacons can be labeled with differently colored fluorophores to detect different target sequences. Any of the probes described herein can be modified and utilized as molecular beacons.

Primer or probe sequences can be ranked according to specific hybridization parameters or metrics that assign a score value indicating their ability to anneal to bacterial strains under highly stringent conditions. Where a primer set is being scored, a "first" or "forward" primer is scored and the "second" or "reverse"-oriented primer sequences can be optimized similarly but with potentially additional parameters, followed by an optional evaluation for primer dimmers, for example, between the forward and reverse primers.

The scoring or ranking steps that are used in the methods of determining the primers and probes include, for example, the following parameters: a target sequence score for the target nucleic acid sequence(s), e.g., the PriMD® score; a mean conservation score for the target nucleic acid sequence(s); a mean coverage score for the target nucleic acid sequence(s); 100% conservation score of a portion (e.g., 5' end, center, 3' end) of the target nucleic acid sequence(s); a species score; a strain score; a subtype score; a serotype score; an associated disease score; a year score; a country of origin score; a duplicate score; a patent score; and a minimum qualifying score. Other parameters that are used include, for example, the number of mismatches, the number of critical mismatches (e.g., mismatches that result in the predicted failure of the sequence to anneal to a target sequence), the number of native strain sequences that contain critical mismatches, and predicted Tm values. The term "Tm" refers to the temperature at which a population of double-stranded nucleic acid molecules becomes half-dissociated into single strands. Methods for calculating the Tm of nucleic acids are known in the art (Berger and Kimmel (1987) *Meth. Enzymol.*, Vol. 152: Guide To Molecular Cloning Techniques, San Diego: Academic Press, Inc. and Sambrook et al. (1989) Molecular Cloning: A Laboratory Manual, (2nd ed.) Vols. 1-3, Cold Spring Harbor Laboratory).

The resultant scores represent steps in determining nucleotide or whole target nucleic acid sequence preference, while tailoring the primer and/or probe sequences so that they hybridize to a plurality of target nucleic acid strains. The methods of determining the primers and probes also can comprise the step of allowing for one or more nucleotide changes when determining identity between the candidate primer and probe sequences and the target nucleic acid strain sequences, or their complements.

In another embodiment, the methods of determining the primers and probes comprise the steps of comparing the candidate primer and probe nucleic acid sequences to "exclusion nucleic acid sequences" and then rejecting those candidate nucleic acid sequences that share identity with the exclusion nucleic acid sequences. In another embodiment, the methods comprise the steps of comparing the candidate primer and probe nucleic acid sequences to "inclusion nucleic acid sequences" and then rejecting those candidate nucleic acid sequences that do not share identity with the inclusion nucleic acid sequences.

In other embodiments of the methods of determining the primers and probes, optimizing primers and probes comprises using a polymerase chain reaction (PCR) penalty score formula comprising at least one of a weighted sum of: primer Tm−optimal Tm; difference between primer Tms; amplicon length−minimum amplicon length; and distance between the primer and a TAQMAN® probe. The optimizing step also can comprise determining the ability of the candidate sequence to hybridize with the most target nucleic acid strain sequences (e.g., the most target organisms or genes). In another embodiment, the selecting or optimizing step comprises determining which sequences have mean conservation scores closest to 1, wherein a standard of deviation on the mean conservation scores is also compared.

In other embodiments, the methods further comprise the step of evaluating which target nucleic acid strain sequences are hybridized by an optimal forward primer and an optimal reverse primer, for example, by determining the number of base differences between target nucleic acid strain sequences in a database. For example, the evaluating step can comprise performing an in silico polymerase chain reaction, involving (1) rejecting the forward primer and/or reverse primer if it does not meet inclusion or exclusion criteria; (2) rejecting the forward primer and/or reverse primer if it does not amplify a medically valuable nucleic acid; (3) conducting a BLAST analysis to identify forward primer sequences and/or reverse primer sequences that overlap with a published and/or patented sequence; (4) and/or determining the secondary structure of the forward primer, reverse primer, and/or target. In an embodiment, the evaluating step includes evaluating whether the forward primer sequence, reverse primer sequence, and/or probe sequence hybridizes to sequences in the database other than the nucleic acid sequences that are representative of the target strains.

The present invention provides oligonucleotides that have preferred primer and probe qualities. These qualities are specific to the sequences of the optimized probes; however, one of ordinary skill in the art would recognize that other molecules with similar sequences could also be used. The oligonucleotides provided herein comprise a sequence that shares at least about 60-70% identity with a sequence described in Tables 2-5. In addition, the sequences can be incorporated into longer sequences, provided they function to specifically anneal to and identify bacterial strains. In another embodiment, the invention provides a nucleic acid comprising a sequence that shares at least about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity with the sequences of Tables 2-5 or complement thereof. The terms "homology" or "identity" or "similarity" refer to sequence relationships between two nucleic acid molecules and can be determined by comparing a nucleotide position in each sequence when aligned for purposes of comparison. The term "homology" refers to the relatedness of two nucleic acid or protein sequences. The term "identity" refers to the degree to which nucleic acids are the same between two sequences. The term "similarity" refers to the degree to which nucleic acids are the same, but includes neutral degenerate nucleotides that can be substituted within a codon without changing the amino acid identity of the codon, as is well known in the art.

In addition, the sequences, including those provided in Table 2 and sequences sharing certain identities with those in Table 2, as described above, can be incorporated into longer sequences, provided they function to specifically anneal to and identify bacterial strains. In one aspect, the longer sequences have 1, 2, 3, 4, 5, 6, 7, 8, 9 or 10 additional bases at either or both ends of the original sequences. These longer sequences are also within the scope of the present disclosure.

The primer and/or probe nucleic acid sequences of the invention are complementary to the target nucleic acid sequence. The probe and/or primer nucleic acid sequences of the invention are optimal for identifying numerous strains of a target nucleic acid, e.g., from pathogens of the GBS species. In an embodiment, the nucleic acids of the invention are primers for the synthesis (e.g., amplification) of target nucleic acid strains and/or probes for identification, isolation, detection, quantitation or analysis of target nucleic acid strains, e.g., an amplified target nucleic acid strain that is amplified using the primers of the invention.

The present oligonucleotides hybridize with more than one bacterial strain (strains as determined by differences in their genomic sequence). The probes and primers provided herein can, for example, allow for the detection and quantitation of currently identified bacterial strains or a subset thereof. In addition, the primers and probes of the present invention, depending on the strain sequence(s), can allow for the detection and quantitation of previously unidentified bacterial strains. In addition, the primers and probes of the present invention, depending on the strain sequence(s), can allow for the detection and quantitation of previously unknown bacterial strains. The methods of the invention provide for optimal primers and probes, and sets thereof, and combinations of sets thereof, which can hybridize with a larger number of target strains than available primers and probes.

In other aspects, the invention also provides vectors (e.g., plasmid, phage, expression), cell lines (e.g., mammalian, insect, yeast, bacterial), and kits comprising any of the sequences of the invention described herein. The invention further provides known or previously unknown target nucleic acid strain sequences that are identified, for example, using the methods of the invention. In an embodiment, the target nucleic acid strain sequence is an amplification product. In another embodiment, the target nucleic acid strain sequence is a native or synthetic nucleic acid. The primers, probes, target nucleic acid strain sequences, vectors, cell lines, and kits can have any number of uses, such as diagnostic, investigative, confirmatory, monitoring, predictive or prognostic.

Diagnostic or screening kits that comprise one or more of the oligonucleotides described herein, which are useful for detecting or screening GBS infection in an individual and/or from a sample, are provided herein. An individual can be a human male, human female, human adult, human child, or human fetus. An individual can also be any mammal, reptile, avian, fish, or amphibian. Hence, an individual can be a primate, pig, horse, cattle, sheep, dog, rabbit, guinea pig, rodent, bird or fish.

A probe of the present invention can comprise a label such as, for example, a fluorescent label, a chemiluminescent label, a radioactive label, biotin, mass tags, gold, dendrimers, aptamer, enzymes, proteins, quenchers and molecular motors. The probe may also be labeled with other similar detectable labels used in conjunction with probe technology as known by one of ordinary skill in the art. In an embodiment, the probe is a hydrolysis probe, such as, for example, a TAQMAN® probe. In other embodiments, the probes of the invention are molecular beacons, any fluorescent probes, and probes that are replaced by any double stranded DNA binding dyes.

Oligonucleotides of the present invention do not only include primers that are useful for conducting the aforementioned amplification reactions, but also include oligonucleotides that are attached to a solid support, such as, for example, a microarray, multiwell plate, column, bead, glass slide, polymeric membrane, glass microfiber, plastic tubes, cellulose, and carbon nanostructures. Hence, detection of GBS strains can be performed by exposing such an oligonucleotide-covered surface to a sample such that the binding of a complementary strain DNA sequence to a surface-attached oligonucleotide elicits a detectable signal or reaction.

Oligonucleotides of the present invention also include primers for isolating, quantitating and sequencing nucleic acid sequences derived from any identified or yet to be isolated and identified GBS genome.

One embodiment of the invention uses solid support-based oligonucleotide hybridization methods to detect gene expression. Solid support-based methods suitable for practicing the present invention are widely known and are described (PCT application WO 95/11755; Huber et al., *Anal. Biochem.*, 299: 24, 2001; Meiyanto et al., *Biotechniques*, 31:406, 2001; Relog10 et al., *Nucleic Acids Res.*, 30:e51, 2002; the contents of which are incorporated herein by reference in their entirety). Any solid surface to which oligonucleotides can be bound, covalently or non-covalently, may be used. Such solid supports include, but are not limited to, filters, polyvinyl chloride dishes, silicon or glass based chips.

In certain embodiments, the nucleic acid molecule can be directly bound to the solid support or bound through a linker arm, which is typically positioned between the nucleic acid sequence and the solid support. A linker arm that increases the distance between the nucleic acid molecule and the substrate can increase hybridization efficiency. There are a number of ways to position a linker arm. In one common approach, the solid support is coated with a polymeric layer that provides linker arms with a plurality of reactive ends/sites. A common example of this type is glass slides coated with polylysine (U.S. Pat. No. 5,667,976, the contents of which are incorporated herein by reference in its entirety), which are commercially available. Alternatively, the linker arm can be synthesized as part of or conjugated to the nucleic acid molecule, and then this complex is bonded to the solid support. One approach, for example, takes advantage of the extremely high affinity biotin-streptavidin interaction. The streptavidin-biotinylated reaction is stable enough to withstand stringent washing conditions and is sufficiently stable that it is not cleaved by laser pulses used in some detection systems, such as matrix-assisted laser desorption/ionization time of flight (MALDI-TOF) mass spectrometry. Therefore, streptavidin can be covalently attached to a solid support, and a biotinylated nucleic acid molecule will bind to the streptavidin-coated surface. In one version of this method, an amino-coated silicon wafer is reacted with the n-hydroxysuccinimido-ester of biotin and complexed with streptavidin. Biotinylated oligonucleotides are bound to the surface at a concentration of about 20 fmol DNA per mm$^2$.

One can alternatively directly bind DNA to the support using carbodiimides, for example. In one such method, the support is coated with hydrazide groups, and then treated with carbodiimide. Carboxy-modified nucleic acid molecules are then coupled to the treated support. Epoxide-based chemistries are also being employed with amine modified oligonucleotides. Other chemistries for coupling nucleic acid molecules to solid substrates are known to those of one of ordinary skill in the art.

In certain embodiments, the nucleic acid molecules, e.g., the primers and probes of the present invention, must be delivered to the substrate material, which is suspected of containing or is being tested for the presence and number of GBS molecules. Because of the miniaturization of the arrays, delivery techniques must be capable of positioning very small amounts of liquids in very small regions, very close to one another and amenable to automation. Several techniques and devices are available to achieve such delivery. Among these are mechanical mechanisms (e.g., arrayers from GeneticMicroSystems, MA, USA) and ink jet technology. Very fine pipets can also be used.

Other formats are also suitable within the context of this invention. For example, a 96-well format with fixation of the nucleic acids to a nitrocellulose or nylon membrane can also be employed.

After the nucleic acid molecules have been bound to the solid support, it is often useful to block reactive sites on the solid support that are not consumed in binding to the nucleic acid molecule. In the absence of the blocking step, excess primers and/or probes can, to some extent, bind directly to the solid support itself, giving rise to non-specific binding. Non-specific binding can sometimes hinder the ability to detect low levels of specific binding. A variety of effective blocking agents (e.g., milk powder, serum albumin or other proteins with free amine groups, polyvinylpyrrolidine) can be used and others are known to those skilled in the art (U.S. Pat. No. 5,994,065, the contents of which are incorporated herein by reference in their entirety). The choice depends at least in part upon the binding chemistry.

One embodiment uses oligonucleotide arrays, e.g., microarrays that can be used to simultaneously observe the expression of a number of GBS strain genes. Oligonucleotide arrays comprise two or more oligonucleotide probes provided on a solid support, wherein each probe occupies a unique location on the support. The location of each probe can be predetermined, such that detection of a detectable signal at a given location is indicative of hybridization to an oligonucleotide probe of a known identity. Each predetermined location can contain more than one molecule of a probe, but each molecule within the predetermined location has an identical sequence. Such predetermined locations are termed features. There can be, for example, from 2, 10, 100, 1,000, 2,000 or 5,000 or more of such features on a single solid support. In one embodiment, each oligonucleotide is located at a unique position on an array at least 2, at least 3, at least 4, at least 5, at least 6, or at least 10 times.

Oligonucleotide probe arrays for detecting gene expression can be made and used according to conventional techniques described (Lockhart et al., *Nat. Biotech.*, 14:1675-1680, 1996; McGall et al., *Proc. Natl. Acad. Sci. USA*, 93:13555, 1996; Hughes et al., *Nat. Biotechnol.*, 19:342, 2001). A variety of oligonucleotide array designs are suitable for the practice of this invention.

Generally, a detectable molecule, also referred to herein as a label, can be incorporated or added to an array's probe nucleic acid sequences. Many types of molecules can be used within the context of this invention. Such molecules include, but are not limited to, fluorochromes, chemiluminescent molecules, chromogenic molecules, radioactive molecules, mass spectrometry tags, proteins, and the like. Other labels will be readily apparent to one skilled in the art.

Oligonucleotide probes used in the methods of the present invention, including microarray techniques, can be generated using PCR. PCR primers used in generating the probes are chosen, for example, based on the sequences of Table 2. In one embodiment, oligonucleotide control probes also are used. Exemplary control probes can fall into at least one of three categories referred to herein as (1) normalization controls, (2) expression level controls and (3) negative controls. In microarray methods, one or more of these control probes can be provided on the array with the inventive cell cycle gene-related oligonucleotides.

Normalization controls correct for dye biases, tissue biases, dust, slide irregularities, malformed slide spots, etc. Normalization controls are oligonucleotide or other nucleic acid probes that are complementary to labeled reference oligonucleotides or other nucleic acid sequences that are added to the nucleic acid sample to be screened. The signals obtained from the normalization controls, after hybridization, provide a control for variations in hybridization conditions, label intensity, reading efficiency and other factors that can cause the signal of a perfect hybridization to vary between arrays. The normalization controls also allow for the semi-quantification of the signals from other features on the microarray. In one embodiment, signals (e.g., fluorescence intensity or radioactivity) read from all other probes used in the method are divided by the signal from the control probes, thereby normalizing the measurements.

Virtually any probe can serve as a normalization control. Hybridization efficiency varies, however, with base composition and probe length. Preferred normalization probes are selected to reflect the average length of the other probes being used, but they also can be selected to cover a range of lengths. Further, the normalization control(s) can be selected to reflect the average base composition of the other probe(s) being used. In one embodiment, only one or a few normalization probes are used, and they are selected such that they hybridize well (i.e., without forming secondary structures) and do not match any test probes. In one embodiment, the normalization controls are bacterial genes.

"Negative control" probes are not complementary to any of the test oligonucleotides (i.e., the GBS-specific marker genes), normalization controls, or expression controls. In one embodiment, the negative control is a bacterial gene which is not complementary to any other sequence in the sample.

The terms "background" and "background signal intensity" refer to hybridization signals resulting from non-specific binding or other interactions between the labeled target nucleic acids (e.g., mRNA present in the biological sample) and components of the oligonucleotide array. Background signals also can be produced by intrinsic fluorescence of the array components themselves. A single background signal can be calculated for the entire array, or a different background signal can be calculated for each target nucleic acid. In one embodiment, background is calculated as the average hybridization signal intensity for the lowest 5 to 10 percent of the oligonucleotide probes being used, or, where a different background signal is calculated for each target gene, for the lowest 5 to 10 percent of the probes for each gene. Where the oligonucleotide probes corresponding to a particular GBS target hybridize well and, hence, appear to bind specifically to a target sequence, they should not be used in a background signal calculation. Alternatively, background can be calculated as the average hybridization signal intensity produced by hybridization to probes that are not complementary to any sequence found in the sample (e.g., probes directed to nucleic acids of the opposite sense or to genes not found in the sample). In microarray methods, background can be calculated as the average signal intensity produced by regions of the array that lack any oligonucleotides probes at all.

In an alternative embodiment, the nucleic acid molecules are directly or indirectly coupled to an enzyme. Following hybridization, a chromogenic substrate is applied and the colored product is detected by a camera, such as a charge-coupled camera. Examples of such enzymes include alkaline phosphatase, horseradish peroxidase and the like. The invention also provides methods of labeling nucleic acid molecules with cleavable mass spectrometry tags (CMST; U.S. Patent Application No. 60/279,890). After an assay is complete, and the uniquely CMST-labeled probes are distributed across the array, a laser beam is sequentially directed to each member of the array. The light from the laser beam both cleaves the unique tag from the tag-nucleic acid molecule conjugate and volatilizes it. The volatilized tag is directed into a mass spectrometer. Based on the mass spectrum of the tag and knowledge of how the tagged nucleotides were prepared, one can unambiguously identify the nucleic acid molecules to which the tag was attached (WO 9905319).

The nucleic acids, primers and probes of the present invention can be labeled readily by any of a variety of techniques. When the diversity panel is generated by amplification, the nucleic acids can be labeled during the reaction by incorporation of a labeled dNTP or use of labeled amplification primer. If the amplification primers include a promoter for an RNA polymerase, a post-reaction labeling can be achieved by synthesizing RNA in the presence of labeled NTPs. Amplified fragments that were unlabeled during amplification or unamplified nucleic acid molecules can be labeled by one of a number of end labeling techniques or by a transcription method, such as nick-translation, random-primed DNA synthesis. Details of these methods are known to one of ordinary skill in the art and are set out in methodology books. Other types of labeling reactions are performed by denaturation of the nucleic acid molecules in the presence of a DNA-binding molecule, such as RecA, and subsequent hybridization under conditions that favor the formation of a stable RecA-incorporated DNA complex.

In another embodiment, PCR-based methods are used to detect gene expression. These methods include reverse-transcriptase-mediated polymerase chain reaction (RT-PCR) including real-time and endpoint quantitative reverse-transcriptase-mediated polymerase chain reaction (Q-RTPCR). These methods are well known in the art. For example, methods of quantitative PCR can be carried out using kits and methods that are commercially available from, for example, Applied BioSystems and Stratagene®. See also Kochanowski, Quantitative PCR Protocols (Humana Press, 1999);

Innis et al., supra.; Vandesompele et al., *Genome Biol.,* 3:RE-SEARCH0034, 2002; Stein, *Cell Mol. Life Sci.* 59:1235, 2002.

The forward and reverse amplification primers and internal hybridization probe is designed to hybridize specifically and uniquely with one nucleotide sequence derived from the transcript of a target gene. In one embodiment, the selection criteria for primer and probe sequences incorporates constraints regarding nucleotide content and size to accommodate TAQMAN® requirements. SYBR Green® can be used as a probe-less Q-RTPCR alternative to the TAQMAN®-type assay, discussed above (ABI Prism® 7900 Sequence Detection System User Guide Applied Biosystems, chap. 1-8, App. A-F. (2002)). This device measures changes in fluorescence emission intensity during PCR amplification. The measurement is done in "real time," that is, as the amplification product accumulates in the reaction. Other methods can be used to measure changes in fluorescence resulting from probe digestion. For example, fluorescence polarization can distinguish between large and small molecules based on molecular tumbling (U.S. Pat. No. 5,593,867).

The primers and probes of the present invention may anneal to or hybridize to various GBS genetic material or genetic material derived therefrom, such as RNA, DNA, cDNA, or a PCR product.

A "sample" that is tested for the presence of GBS strains includes, but is not limited to a tissue sample, such as, for example, blood, serum, plasma, enriched peripheral blood mononuclear cells, fecal material, urine, neoplastic or other tissue obtained from biopsies, cerebrospinal fluid, saliva, fluids collected from the ear, eye, mouth, and respiratory airways, sputum, stool, skin, gastric secretions, oropharyngeal swabs, nasopharyngeal swabs, throat swabs, rectal swabs, peri-rectal swabs, vaginal swabs, nasal aspirates, nasal wash, renal tissue, and fluid therefrom including perfusion media, pure cultures of bacterial fungal isolates, fluids and cells obtained by the perfusion of tissues of both human and animal origin, and fluids and cells derived from the culturing of human cells, including human stem cells and human cartilage or fibroblasts, pure cultures of bacterial fungal isolates, and swabs or washes of environmental surfaces, or other samples derived from environmental surfaces. In a particular embodiment, the sample is from a human, is non-human in origin, or is derived from an inanimate object. The tissue sample may be fresh, fixed, preserved, or frozen.

The target nucleic acid strain that is amplified may be RNA or DNA or a modification thereof. Thus, the amplifying step can comprise isothermal or non-isothermal reactions, such as polymerase chain reaction, SCORPION™ primers, molecular beacons, SIMPLEPROBES®, HyBeacons®, cycling probe technology, INVADER® Assay, self-sustained sequence replication, nucleic acid sequence-based amplification, ramification amplifying method, hybridization signal amplification method, rolling circle amplification, multiple displacement amplification, thermophilic strand displacement amplification, transcription-mediated amplification, ligase chain reaction, signal mediated amplification of RNA, split promoter amplification, Q-Beta replicase, isothermal chain reaction, one cut event amplification, loop-mediated isothermal amplification, molecular inversion probes, ampliprobe, headloop DNA amplification, and ligation activated transcription. The amplifying step can be conducted on a solid support, such as a multiwell plate, array, column, bead, glass slide, polymeric membrane, glass microfiber, plastic tubes, cellulose, and carbon nanostructures. The amplifying step also comprises in situ hybridization. The detecting step can comprise gel electrophoresis, fluorescence resonant energy transfer, or hybridization to a labeled probe, such as a probe labeled with biotin, at least one fluorescent moiety, an antigen, a molecular weight tag, and a modifier of probe Tm. The detection step can also comprise the incorporation of a label (e.g., fluorescent or radioactive) during an extension reaction. The detecting step comprises measuring fluorescence, mass, charge, and/or chemiluminescence.

The target nucleic acid strain may not need amplification and may be RNA or DNA or a modification thereof. If amplification is not necessary, the target nucleic acid strain can be denatured to enable hybridization of a probe to the target nucleic acid sequence.

Hybridization may be detected in a variety of ways and with a variety of equipment. In general, the methods can be categorized as those that rely upon detectable molecules incorporated into the diversity panels and those that rely upon measurable properties of double-stranded nucleic acids (e.g., hybridized nucleic acids) that distinguish them from single-stranded nucleic acids (e.g., unhybridized nucleic acids). The latter category of methods includes intercalation of dyes, such as, for example, ethidium bromide, into double-stranded nucleic acids, differential absorbance properties of double and single stranded nucleic acids, binding of proteins that preferentially bind double-stranded nucleic acids, and the like.

EXEMPLIFICATION

Example 1

Scoring a Set of Predicted Annealing Oligonucleotides

Each of the sets of primers and probes selected is ranked by a combination of methods as individual primers and probes and as a primer/probe set. This involves one or more methods of ranking (e.g., joint ranking, hierarchical ranking, and serial ranking) where sets of primers and probes are eliminated or included based on any combination of the following criteria, and a weighted ranking again based on any combination of the following criteria, for example: (A) Percentage Identity to Target Variants; (B) Conservation Score; (C) Coverage Score; (D) Strain/Subtype/Serotype Score; (E) Associated Disease Score; (F) Duplicates Sequences Score; (G) Year and Country of Origin Score; (H) Patent Score, and
(I) Epidemiology Score.
(A) Percentage Identity A percentage identity score is based upon the number of target nucleic acid variant (e.g., native) sequences that can hybridize with perfect conservation (the sequences are perfectly complementary) to each primer or probe of a primer pair and probe set. If the score is less than 100%, the program ranks additional primer pair and probe sets that are not perfectly conserved. This is a hierarchical scale for percent identity starting with perfect complementarity, then one base degeneracy through to the number of degenerate bases that would provide the score closest to 100%. The position of these degenerate bases would then be ranked. The methods for calculating the conservation is described under section B.

(i) Individual Base Conservation Score

A set of conservation scores is generated for each nucleotide base in the consensus sequence and these scores represent how many of the target nucleic acid variants sequences have a particular base at this position. For example, a score of 0.95 for a nucleotide with an adenosine, and 0.05 for a nucleotide with a cytidine means that 95% of the native sequences have an A at that position and 5% have a C at that position. A perfectly conserved base position is one where all the target nucleic acid variant sequences have the same base (either an A, C, G, or T/U) at that position. If there are an equal number of bases (e.g., 50% A & 50% T) at a position, it is identified with an N.

(ii) Candidate Primer/Probe Sequence Conservation

An overall conservation score is generated for each candidate primer or probe sequence that represents how many of the target nucleic acid variant sequences will hybridize to the primers or probes. A candidate sequence that is perfectly complimentary to all the target nucleic acid variant sequences will have a score of 1.0 and rank the highest. For example, illustrated below in Table 1 are three different 10-base candidate probe sequences that are targeted to different regions of a consensus target nucleic acid variant sequence. Each candidate probe sequence is compared to a total of 10 native sequences.

TABLE 1

| #1. | A | A | A | C | A | C | G | T | G | C |
|---|---|---|---|---|---|---|---|---|---|---|
|  | 0.7 | 1.0 | 1.0 | 1.0 | 1.0 | 1.0 | 1.0 | 1.0 | 1.0 | 1.0 |

SEQ ID NO: 65
→Number of target nucleic acid variant sequences that are perfectly complimentary - 7. Three out of the ten sequences do not have an A at position 1.

| #2. | C | C | T | T | G | T | T | C | C | A |
|---|---|---|---|---|---|---|---|---|---|---|
|  | 1.0 | 0.9 | 1.0 | 0.9 | 0.9 | 1.0 | 1.0 | 1.0 | 1.0 | 1.0 |

SEQ ID NO: 66
→Number of target nucleic acid variant sequences that are perfectly complimentary - 7, 8, or 9. At least one target nucleic acid variant does not have a C at position 2, T at position 4, or G at position 5. These differences may all be on one target nucleic acid variant molecule or may be on two or three separate molecules.

| #3. | C | A | G | G | G | A | C | G | A | T |
|---|---|---|---|---|---|---|---|---|---|---|
|  | 1.0 | 1.0 | 1.0 | 1.0 | 1.0 | 0.9 | 0.8 | 1.0 | 1.0 | 1.0 |

SEQ ID NO: 67
→Number of target nucleic acid variant sequences that are perfectly complimentary - 7 or 8. At least one target nucleic acid variant does not have an A at position 6 and at least two target nucleic acid variant do not have a C at position 7. These differences may all be on one target nucleic acid variant molecule or may be on two separate molecules.

A simple arithmetic mean for each candidate sequence would generate the same value of 0.97. The number of target nucleic acid variant sequences identified by each candidate probe sequence, however, can be very different. Sequence #1 can only identify 7 native sequences because of the 0.7 (out of 1.0) score by the first base—A. Sequence #2 has three bases each with a score of 0.9; each of these could represent a different or shared target nucleic acid variant sequence. Consequently, Sequence #2 can identify 7, 8 or 9 target nucleic acid variant sequences. Similarly, Sequence #3 can identify 7 or 8 of the target nucleic acid variant sequences. Sequence #2 would, therefore, be the best choice if all the three bases with a score of 0.9 represented the same 9 target nucleic acid variant sequences.

(iii) Overall Conservation Score of the Primer and Probe Set—Percent Identity

The same method described in (ii) when applied to the complete primer pair and probe set will generate the percent identity for the set (see A above). For example, using the same sequences illustrated above, if Sequences #1 and #2 are primers and Sequence #3 is a probe, then the percent identity for the target can be calculated from how many of the target nucleic acid variant sequences are identified with perfect complimentarity by all three primer/probe sequences. The percent identity could be no better than 0.7 (7 out of 10 target nucleic acid variant sequences) but as little as 0.1 if each of the degenerate bases reflects a different target nucleic acid variant sequence. Again, an arithmetic mean of these three sequences would be 0.97. As none of the above examples were able to capture all the target nucleic acid variant sequences because of the degeneracy (scores of less than 1.0), the ranking system takes into account that a certain amount of degeneracy can be tolerated under normal hybridization conditions, for example, during a polymerase chain reaction. The ranking of these degeneracies is described in (iv) below.

An in silico evaluation determines how many native sequences (e.g., original sequences submitted to public databases) are identified by a given candidate primer/probe set. The ideal candidate primer/probe set is one that can perform PCR and the sequences are perfectly complimentary to all the known native sequences that were used to generate the consensus sequence. If there is no such candidate, then the sets are ranked according to how many degenerate bases can be accepted and still hybridize to just the target sequence during the PCR and yet identify all the native sequences.

The hybridization conditions, for TAQMAN® as an example are: 10-50 mM Tris-HCl pH 8.3, 50 mM KCl, 0.1-0.2% Triton® X-100 or 0.1% Tween®, 1-5 mM $MgCl_2$. The hybridization is performed at 58-60° C. for the primers and 68-70° C. for the probe. The in silico PCR identifies native sequences that are not amplifiable using the candidate primers and probe set. The rules can be as simple as counting the number of degenerate bases to more sophisticated approaches based on exploiting the PCR criteria used by the PriMD® software. Each target nucleic acid variant sequence has a value or weight (see Score assignment above). If the failed target nucleic acid variant sequence is medically valuable, the primer/probe set is rejected. This in silico analysis provides a degree of confidence for a given genotype and is important when new sequences are added to the databases. New target nucleic acid variant sequences are automatically entered into both the "include" and "exclude" categories. Published primer and probes will also be ranked by the PriMD® software.

(iv) Position (5' to 3') of the Base Conservation Score

In an embodiment, primers do not have bases in the terminal five positions at the 3' end with a score less than 1. This is one of the last parameters to be relaxed if the method fails to select any candidate sequences. The next best candidate having a perfectly conserved primer would be one where the poorer conserved positions are limited to the terminal bases at the 5' end. The closer the poorer conserved position is to the 5' end, the better the score. For probes, the position criteria is different. For example, with a TAQMAN® probe, the most destabilizing effect occurs in the center of the probe. The 5' end of the probe is also important as this contains the reporter molecule that must be cleaved, following hybridization to the target, by the polymerase to generate a sequence-specific signal. The 3' end is less critical. Therefore, a sequence with a perfectly conserved middle region will have the higher score. The remaining ends of the probe are ranked in a similar fashion to the 5' end of the primer. Thus, the next best candidate to a perfectly conserved TAQMAN® probe would be one where the poorer conserved positions are limited to the terminal bases at either the 5' or 3' ends. The hierarchical scoring will select primers with only one degeneracy first, then primers with two degeneracies next and so on. The relative position of each degeneracy will then be ranked favoring those that are closest to the 5' end of the primers and those closest to the 3' end of the TAQMAN® probe. If there are two or more degenerate bases in a primer and probe set the ranking will initially select the sets where the degeneracies occur on different sequences.

B. Coverage Score

The total number of aligned sequences is considered under coverage score. A value is assigned to each position based on how many times that position has been reported or sequenced. Alternatively, coverage can be defined as how representative the sequences are of the known strains, subtypes etc., or their relevance to a certain diseases. For example, the target nucleic acid variant sequences for a particular gene may be very well conserved and show complete coverage but certain strains are not represented in those sequences.

A sequence is included if it aligns with any part of the consensus sequence, which is usually a whole gene or a functional unit, or has been described as being a representative of this gene. Even though a base position is perfectly conserved it may only represent a fraction of the total number of sequences (for example, if there are very few sequences). For example, region A of a gene shows a 100% conservation from 20 sequence entries while region B in the same gene shows a 98% conservation but from 200 sequence entries. There is a relationship between conservation and coverage if the sequence shows some persistent variability. As more sequences are aligned, the conservation score falls, but this effect is lessened as the number of sequences gets larger. Unless the number of sequences is very small (e.g., under 10) the value of the coverage score is small compared to that of the conservation score. To obtain the best consensus sequence, artificial spaces are allowed to be introduced. Such spaces are not considered in the coverage score.

C. Strain/Subtype/Serotype Score

A value is assigned to each strain or subtype or serotype based upon its relevance to a disease. For example, strains of GBS that are linked to high frequencies of infection will have a higher score than strains that are generally regarded as benign. The score is based upon sufficient evidence to automatically associate a particular strain with a disease. For example, certain strains of adenovirus are not associated with diseases of the upper respiratory system. Accordingly, there will be sequences included in the consensus sequence that are not associated with diseases of the upper respiratory system.

D. Associated Disease Score

The associated disease score pertains to strains that are not known to be associated with a particular disease (to differentiate from D above). Here, a value is assigned only if the submitted sequence is directly linked to the disease and that disease is pertinent to the assay.

E. Duplicate Sequences Score

If a particular sequence has been sequenced more than once it will have an effect on representation, for example, a strain that is represented by 12 entries in GENBANK® genetic sequence database of which six are identical and the other six are unique. Unless the identical sequences can be assigned to different strains/subtypes (usually by sequencing other gene or by immunology methods) they will be excluded from the scoring.

F. Year and Country of Origin Score

The year and country of origin scores are important in terms of the age of the human population and the need to provide a product for a global market. For example, strains identified or collected many years ago may not be relevant today. Furthermore, it is probably difficult to obtain samples that contain these older strains. Certain divergent strains from more obscure countries or sources may also be less relevant to the locations that will likely perform clinical tests, or may be more important for certain countries (e.g., North America, Europe, or Asia).

G. Patent Score

Candidate target variant sequences published in patents are searched electronically and annotated such that patented regions are excluded. Alternatively, candidate sequences are checked against a patented sequence database.

H. Minimum Qualifying Score

The minimum qualifying score is determined by expanding the number of allowed mismatches in each set of candidate primers and probes until all possible native sequences are represented (e.g., has a qualifying hit).

I. Other

A score is given to based on other parameters, such as relevance to certain patients (e.g., pediatrics, immunocompromised) or certain therapies (e.g., target those strains that respond to treatment) or epidemiology. The prevalence of an organism/strain and the number of times it has been tested for in the community can add value to the selection of the candidate sequences. If a particular strain is more commonly tested then selection of it would be more likely. Strain identification can be used to select better vaccines.

Example 2

Primer/Probe Evaluation

Once the candidate primers and probes have received their scores and have been ranked, they are evaluated using any of a number of methods, such as, for example, BLAST™ sequence alignment tool analysis and secondary structure analysis.

A. BLAST Analysis

The candidate primer/probe sets are submitted to BLAST™ sequence alignment tool analysis to check for possible overlap with any published sequences that might be missed by the Include/Exclude function. It also provides a useful summary.

B. Secondary Structure

The methods of the present invention include analysis of nucleic acid secondary structure. This includes the structures of the primers and/or probes as well as their intended target variant sequences. The methods and software of the invention predict the optimal temperatures for the annealing but assumes that the target (e.g., RNA or DNA) does not have any significant secondary structure. For example, if the starting material is RNA, the first stage is the creation of a complimentary strand of DNA (cDNA) using a specific primer. This is usually performed at temperatures where the RNA template can have significant secondary structure thereby preventing the annealing of the primer. Similarly, after denaturation of a double stranded DNA target (for example, an amplicon after PCR), the binding of the probe is dependent on there being no major secondary structure in amplicon.

The methods of the invention can either use this information as a criteria for selecting primers and probes or evaluate any secondary structure of a selected sequence, for example, by cutting and pasting candidate primer or probe sequences into a commercial internet link that uses software dedicated to analyzing secondary structure, such as, for example, MFOLD (Zuker et al. (1999) Algorithms and Thermodynamics for RNA Secondary Structure Prediction: A Practical Guide in RNA Biochemistry and Biotechnology, J. Barciszewski and B. F. C. Clark, eds., NATO ASI Series, Kluwer Academic Publishers).

C. Evaluating the Primer and Probe Sequences

The methods and software of the invention may also analyze any nucleic acid sequence to determine its suitability in a nucleic acid amplification-based assay. For example, it can accept a competitor's primer set and determine the following information: (1) How it compares to the primers of the invention (e.g., overall rank, PCR and conservation ranking, etc.); (2) How it aligns to the exclude libraries (e.g., assessing cross-hybridization)—also used to compare primer and probe sets to newly published sequences; and (3) If the sequence has been previously published. This step requires keeping a database of sequences published in scientific journals, posters, and other presentations.

Example 3

Multiplexing

The Exclude/Include capability is ideally suited for designing multiplex reactions. The parameters for designing multiple primer and probe sets adhere to a more stringent set of parameters than those used for the initial Exclude/Include function. Each set of primers and probe, together with the resulting amplicon is screened against the other sets that constitute the multiplex reaction. As new targets are accepted their sequences are automatically added to the Exclude category.

The database is designed to interrogate the online databases to determine and acquire, if necessary, any new sequences relevant to the targets. These sequences are evaluated against the optimal primer/probe set. If they represented a new genotype or strain then a multiple sequence alignment may be required.

Example 4

Sequences Identified for Detecting the GBS Genes neuA and/or cspA and/or cylE and/or hylB and/or mreA and/or ptsI The set of primers and probes were then scored according to the methods described herein to identify the optimized primers and probes of Tables 2 and 4. It should be noted that the primers, as they are sequences that annual to a plurality of all identified or unidentified GBS strains, can also be used as probes either in the presence or absence of amplification of a sample.

TABLE 2

Optimized Primers and Probes for Detecting Group B *Streptococcus*.

| Group No. | Forward Primer | Probe | Reverse Primer |
|---|---|---|---|
| | | neuA | |
| 1 | SEQ ID NO: 1 TCCTTTGCCATTTGATAAGCATATG | SEQ ID NO: 2 AGGTTATCGTCGCCAAGATTTACAAC | SEQ ID NO: 3 TGCTATAGATATGGTGGGAGCAGAT |
| | | cspA | |
| 2 | SEQ ID NO: 4 ACTGCCTTAATGACTACAAGTTCAG | SEQ ID NO: 5 CCTATCTACTCAACAGACGGTACTAGTCC | SEQ ID NO: 6 TAGACTTATAGCTTCCCAAGGCTTT |
| 3 | SEQ ID NO: 4 ACTGCCTTAATGACTACAAGTTCAG | SEQ ID NO: 5 CCTATCTACTCAACAGACGGTACTAGTCC | SEQ ID NO: 7 TATAGCTTCCCAAGGCTTTCAATTG |
| 4 | SEQ ID NO: 8 TCTAAGCCACAACAAATGGTGTTTG | SEQ ID NO: 9 TGTTAGTGTAGGAGCTTGTCTATCCAAAGTGATAT | SEQ ID NO: 10 ACGTCTATCTTTGTCATAAGTTGCT |
| | | cylE | |
| 5 | SEQ ID NO: 11 CGTAGTCACCTCCCTAAGATATTGA | SEQ ID NO: 12 CCTAATTTCTGTCTCCTCTTCCAAGG | SEQ ID NO: 13 ATATTTCTTCATCAGAGACTTTGGT |
| | | hylB | |
| 6 | SEQ ID NO: 14 TTACTACTGCTACTAAAGCTGAAGG | SEQ ID NO: 15 CATCTATCAGAACATTACCATAGGCGC | SEQ ID NO: 16 TGATAGGCAGCAATTGTGTCAAAC |
| 7 | SEQ ID NO: 14 TTACTACTGCTACTAAAGCTGAAGG | SEQ ID NO: 17 AGAACATTACCATAGGCGCCAGT | SEQ ID NO: 18 GCAATTGTGTCAAACCATCTATC |
| | | mreA | |
| 8 | SEQ ID NO: 19 TCGTCTTAACGTTTAATGAGACACC | SEQ ID NO: 20 TCGTCTAACCTTCGCTCGCTTCCAAC | SEQ ID NO: 21 TAACTCATCGACGCCATACTCTTGA |
| | | ptsI | |
| 9 | SEQ ID NO: 22 CCATACAATCCATCAATCCTTCGTT | SEQ ID NO: 23 TTGATCACCGGCCATCTCACCACACAT | SEQ ID NO: 24 CATACCAACAAGAAGTGGAACCG |
| 10 | SEQ ID NO: 25 CTGAAGGTAAATGGGCAGGTATG | SEQ ID NO: 26 TGAGATGGCCGGTGATCAAACTGCG | SEQ ID NO: 27 TAAGCTACGTGTACGAAGTACTGAG |

TABLE 2-continued

Optimized Primers and Probes for Detecting Group B *Streptococcus*.

| Group No. | Forward Primer | Probe | Reverse Primer |
|---|---|---|---|
| 11 | SEQ ID NO: 22<br>CCATACAATCCATCAATCCTTCGTT | SEQ ID NO: 28<br>CGCAGTTTGATCACCGGCCATCTC | SEQ ID NO: 29<br>AATCCCATACCAACAAGAAGTGGA |
| 12 | SEQ ID NO: 30<br>AGCAAGTTTCATACCTCTATCAACC | SEQ ID NO: 31<br>CCGGCCATCTCCACCACACATACCTG | SEQ ID NO: 32<br>GAAGTGGAACCGCAGTTTGATC |
| 13 | SEQ ID NO: 33<br>GCAGAAGAAGCTCGCCTTGA | SEQ ID NO: 34<br>TGCACTCCAAGCTTCACAAGACGAGC | SEQ ID NO: 35<br>TCAAATACAGCTGCGGCTTCTC |

TABLE 3

GBS Gene Sequence for Positive Control

GBS Gene Sequence for Positive Control

SEQ ID NO: 36
TCCTTTGCCATTTGATAAGCATATGTCCTAGAGGTGAAAAAGCTTTTTTC

CCTTAAGTAAGTTTCTTTATTAGAAATAAAAATAGCGCCGTTCGGATAGT

ATAAAGGTTGTAAATCTTGGCGACGATAACCTTTATCTGCTCCCACCATA

TCTATAGCA

TABLE 4

Primers and Probes for Detecting *Geobacillus stearothermophilus* (Process Control).

| Group No. | Forward Primer | Probe | Reverse Primer |
|---|---|---|---|
| 14 | SEQ ID NO: 37<br>TTTTCATTTGCTCAAAATCAACC | SEQ ID NO: 38<br>GAGCCGATCACTGTCCGTCCGG | SEQ ID NO: 39<br>AGTTGCAGCGCATTATTTTAAAAGG |
| 15 | SEQ ID NO: 40<br>GTGGAAACGATCCGGAATGC | SEQ ID NO: 41<br>AAATGTATGGTGTGGGATACAGAGAAG | SEQ ID NO: 42<br>CGATCAGTTGCTTGACATGTTCAT |
| 16 | SEQ ID NO: 43<br>TCAACTTCCGGCGTGATGA | SEQ ID NO: 44<br>TATCCCGCTCCCAATAATGCGACGACG | SEQ ID NO: 45<br>GATCACGACGTTGGAAAACTTCAC |
| 17 | SEQ ID NO: 46<br>TCGGAATGCGCATTTCATCAATG | SEQ ID NO: 47<br>CCGGGAAGATGTCATCGGCGC | SEQ ID NO: 48<br>TGAGCCCGATCATGAATACGATC |
| 18 | SEQ ID NO: 46<br>TCGGAATGCGCATTTCATCAATG | SEQ ID NO: 47<br>CCGGGAAGATGTCATCGGCGC | SEQ ID NO: 49<br>CTCGCCGATTTACAAAATGAT |
| 19 | SEQ ID NO: 46<br>TCGGAATGCGCATTTCATCAATG | SEQ ID NO: 47<br>CCGGGAAGATGTCATCGGCGC | SEQ ID NO: 50<br>TCGCCGATTTACAAAATGATCGTC |
| 20 | SEQ ID NO: 46<br>TCGGAATGCGCATTTCATCAATG | SEQ ID NO: 47<br>CCGGGAAGATGTCATCGGCGC | SEQ ID NO: 51<br>GGCATCCCAGACGAATGG |
| 21 | SEQ ID NO: 46<br>TCGGAATGCGCATTTCATCAATG | SEQ ID NO: 47<br>CCGGGAAGATGTCATCGGCGC | SEQ ID NO: 52<br>CAGCGCTCGCCGATT |
| 22 | SEQ ID NO: 53<br>GCGAATGCGAGCGAACAA | SEQ ID NO: 54<br>CTCCAAAAGGCCGCCAATCCACAT | SEQ ID NO: 55<br>GTGTGAAGATGCAATAACGGTTTTC |
| 23 | SEQ ID NO: 56<br>TATTCGATCGGAATGCGCATTTCA | SEQ ID NO: 57<br>CAAGCGAGCGCCGATGACATCTTC | SEQ ID NO: 58<br>CGATCATGAATACGATCGAAGGAAA |

TABLE 5

Target gene sequences for *Geobacillus stearothermophilus* (Process Control)

*Geobacillus stearothermophilus* Target Gene Sequences for Process Control

SEQ ID NO: 59
TTTTTAGGAAACCGGCTTGTGCCAAGATCAATGTTTTTTTATTTGGACAACTCCATGAGCAAATCGCCTGCCTGGATCGCATCG
CCGCTTTTGACGTAAATGTCTTTGACAACACCGGCAAACGGTGCTTGCACGGTCGTTTCCATTTTCATTGCTTCCGTGACCATT
AAATGGTCCCCTTTGTCGACTTTTTCCCCTTTTTCGACAAGGCACTTTAACAACCGTACCCGGCATCGTCGCCGCAATATGGTTC
GGGTTCGTCCGATCCGCTTTAATGTGCTCAACGACTGCGGTTTTAATGCTTTCATCGCGGATGACAACTTCACGCGGTTGACCG
TTCAGCTCGAAGTAGACGACGCGTGTACCGTCCGCCTGCGGCTGGCCGATCGACACAAGCTTAACGATCAACGTTTTTCCGCG
CTCGATTTCCACTTCAATTTCCTCGCCAAGGCGCATGCCATACAAGAACGTCGGTGTATCGAGTACAGACACATCGCCGTATT
TTTCCACCGTTTCTGCATATTCAAGAAACACTTTCGGATAAAGGGCGTACGCAATGGCATCAAAGTCGGTCACTTCGCGGCCA
AGCTTGTCATACAGCTCTTTTTTCATTTGCTCAAAATCAACCGGCTCGAGCAGTTCCCCCGGACGGACAGTGATCGGCTCGCG
TCCTTTTAAAATAATGCGCTGCAACTCTTTCGGGAATCCGCCGTGCGGCTGGCCTAAATATCCTTCAAACAGCTCGACGACTG
AATCAGGGAAGTTCAGCGTTTCGCCGCGCTCGAAAATGTCTTGTTCCGTCAAGTTGTTTTGCACCATGTAAAGCGCCATATCG
CCGACGACTTTCGATGACGGCGTCACTTTGACAATATCGCCGAACAAGTCGTTGACGCGGCGGTACATTTCTTTCACTTCATC
CCACCGATCGCCGAGACCGACCGCTTTCGCCTGCTGCTGCAAGTTGCTGTATTGACCGCCTGGCATTTCGTGCATGTACACTTC
CGTATGCGGCGCGTTCATGCCGCTTTCAAATTCTTGATAAAACTTGCGCACATCTTCCCAATAGCGCGCTAACTGCTCAAGAC
CGTAAATGTCGACTTCCGGCGCCCGCTCGGTCCCTTCAAGCGCATAGTAAAGCGTATTGGCGCTCGGCTGAGACGTTAAGCCG
GCCATCGAACTGATGGCGACATCAACAATATCAACGCCGGCTTCAATCGCTTTCGCGTACGTATAAATGCCGTTACCGCTCGT
GTCGTGCGTATGCAAATAAATCGGAATGTCGACTGTTTCCTTGAGCCCGGAAATGAGCACATGCGCCGCCTGCGGCTTCAAGA
GCCCCGCCATATCTTTAATGGCCAAAATGTGCGCACCCGCCTGTTCAAGCTCTTTCGCAAGGGCCTTATAGTAATCCAAATTG
TATTTCGACCGGCTCGGATCTAAAATATCACCCGTATAGCAAATCGCCGCTTCAGCGATTTTGCCGCTCTGCCGGACGGCGTC
GATCGCCACCGTCATTCCTTTCACCCAGTTTAAACTGTCGAAAATTCGGAACACATGGATGCCAGCATGCGCCGATTTTCGA
CGAACTCGCGGATGACGTTGTCCGGATAGTTTTTGTAGCCTACGGCGTTGGCAGAACGGGAGCAACATTTGGAACAACACGTT
GGGAATGCGTCGCGCAGCTTCAGAAGCCGATCCCACGGATCCTCTTTTAAAAAGCGATACGCCACATCAAACGTCGCCCCGC
CCCACATTTCAAGCGAGAATAAATTCGGCAATAAGCGCGCGCTCGGCTCGGCTGCACGCACTAAATGACCGTGCGGACTCG
TGTCGCCAACAGTGACTGATGAGCGTCCCGGAACGTCGTATCGGTCAAGAGCACCCGCGGCTGTTCTTGAATCCAGCGGACA
AGCCCCTCGGGGCCATGCTTGTCCAAAATTTGCTTCGTTCCGGCCCGGGATCGGCTCTGCCTCGCTCAATTTTGGCAAGCGCGG
CTTGTCAAACACCGGCTTTTTCTTTTTGCCGATGCCTGGGAATCCATTGACCGTCACTGTGCCGATGTAAGTGAGCATTTTCGT
TCCGCGGTCTTTCCGGCGTGGGAACACGAATAGTTCCGGCGTCGTATCGATGAACGACGTATCGTATTCGCCTGATAAAAACT
TCGGATGTTGGACGACATTTTCCAAGAACGGAATGTTCGTTTTAAATACGCGAATGCGGAACGTCCGCAAGTTGCGCAGCATT
TTTCTTGCTGCCTGCTCAAACGTCAACGCCCATGTCGACAATTTGACGAGCAAGGAATCGTAATACGGCGTAATGACTGCCCC
TTGGAAACCGTTGCCGGCGTCAAACGTACACCAAAGCCCCCACCGGAGCGGATACGCCATTATTTTCCCAGTATCTGGCATAA
AGTTATTGAGCGGGTCTTCCGTCGTCACCCGCGACTGAATGGCATAACCGTTAATGCGGATGTCTTCCTGCTTCGGAATGCCG
ACTTCATGGCTATGAAGCGAACAGCCATCAGCAATTAAAATTTGCGACTGGACGATATCAATTCCAGTAATCATCTCGGTGAT
CGTATGCTCGACTTGAATGCGCGGGTTGACTTCGATGAAATAAAACTCATCACCCGAAACGAGAAATTCGACCGTGCCGGCA
TTGACATAACCGACGCTTCTCATAAGCTGAACCGCTGCCTCGCAAATGCGTTGGCGCAGCTCGTCCGACAGCGAGACGCTCGG
CGCGACTTCGACGACTTTTTGGTGGCGGCGCTGCACCGAGCAGTCGCGTTCATAAAGGTGAACGATATTTCCTTCATAGTCAC
CTAAAATTTGCACTTCAATGTGCTTTGGATTTTCGATCAACTTTTCAACATACACCTCATCGCTGCCAAACGCCGCTTTTGCTT
CCGATTTGGCACGCTCAAACGCTTCTTTAACTTCCGACTTCGAACGGACGAATCGCATGCCGCGCCCACCGCGCCAAGTGCT
GCTTTAATGATGATCGGATAGCCGTGCGCTTCGGCGAAAGCGACAACTCCTCAAGGCCGTCGACCGGCCCGTCGCTGCCCG
GAATGACCGGAATGCCAGCGTTCACCGCCGCATGGCGCGCTTTCACCTTGTCGCCGAACATGTCCAAATGGTTCTCATTCGGG
CCAAAAAAATAATTCCTTCTTCACGGCACCGTTTAGCAAATTGAATATTTTCTGAAAAAAACCCATATCCTGGGTGAATCGC
ATCGACATCGTGGGCCTTGGCAATCTCAATGATGCCTTCAATATCCAAATACGCCTCAATCGGCTTTTTTCCTTCACCGACTAA
ATACGCTTCATCCGCTTTATAGCGGTGGTATGAGCCGACATCTTCCTTCGAGTAAATGGCCACGGTGCGGATGCCAAGCTCCG
TGCAGGCGCGGAAAACGCGGATGGCGATCTCCCCGCGGTTAGCTACGAGCACTTTGCGAATTCGTCTTGTCTTCATCGTCTTT
CCTCCTTTCTAATTTAAACTATAAAACTTTTTCTATTTTGTAAATACACTTTCTAAAAAGTCAGACCTCTTTT

SEQ ID NO: 60
AGCCATCCACCACCGCTCAACCGACCATTTCGCTTATGCTTATGACAGCGAGACGCTCCATCTCCGGCTTCAAACAAAGAAAC
ATGATGTCGACCACGTCGAGCTGCTTTTTGGCGACCCGTACGAATGGCACGATGGCGCCTGGCAGTTTCAAACGATGCCGATG
CGGAAAACGGGAAGCGACGGGTTGTTTGACTATTGGCTCGCCGAAGTCAAACCGCCATATCGACGGCTGCGCTATGGGTTTG
TGCTTCGAGCTGGGGACGAGAAACTGGTCTATACGGAAAAAGGATTTTACCATGAAGCTCCGAGCGACGACACCGCTTACTA
CTTTTGCTTCCCCTTTCTTCATCGGGTCGACCTATTCCAAGCGCCGGACTGGGTAAAAGACACAGTATGGTATCAAATTTTCCC
CGAGCGGTTCGCCAACGGCAACCCGGCCATCAGTCCGAAAGGGGCGCGGCCGTGGGGAAGCGAGGACCCGACGCCGACGAG
CTTTTTCGGCGGCGACTTGCAAGGAATCATCGATCACCTTGACTATTTGGCTGATCTCGGCATCACCGGCATTTACTTGACGCC
GATTTTCCGCGCGCCGTCGAATCATAAATACGACACCGCTGATTATTTTGAAATCGACCCACTTTGGGGACAAAGAGACGT
TGAAAACACTTGTCAAGCGCTGCCATGAAAAAGGGATCCGCGTCATGCTCGATGCAGTCTTCAATCATTGCGGCTATGAGTTT
GCCCCGTTTCAAGATGTGTTAAAAAACGGTGCAGCGTCTAGGTATAAAGATTGGTTCCATATTCGCGAGTTTCCGCTCCAAAC
GGAGCCGCGCCCGAATTACGACACATTTGCGTTCGTGCCGCAAATGCCCAAACTCAATACCGCCCATCCGGAAGTGAAGCGC
TACTTGCTTGATGTCGCGACGTACTGGATTCGCGAGTTTGATATTGACGGCTGGCGGCTCGATGTGGCAAACGAAATCGATCA
CCAATTTTGGCGCGAATTCCGTCAGGCGGTGAAGGCGCTAAAGCCCGATGTGTACATTCTCGGCGAGATTTGGCATGATGCCA
TGCCGTGGCTGCGCGGCGACCAATTTGACGCCGTCATGAACTACCCGTTCACGGACGGAGCGCTTCGCTTTTTCGCGAAAGAG
GAAATCAGCGCCCGCCAGTTTGCCGATATCATGGTCCGGTTGCTTCATTCGTATCCGAAACATGTGAACGAAGCGGCGTTTAA
CTTGCTTGGCAGCCATGATACACCAAGGCTGCTCACTGTTTGCGGCGGCGACGTCCGCAAAGCGAAGTTGTTGTTTTGTTCC
AGCTCACGTTCACTGGTTCGCCGTGTATTTACTATGGCGATGAGATCGGCGGTGGAAACGATCCGGAATGCCGGAA
ATGTATGGTGTGGGATACAGAGAAGCAAAACAAAGAACTGTATGAACATGTCAAGCAACTGATCGCTCTTCGCAGGCAATAT
CGGGCGCTTCGACGCGGCGATGTCGCTTTTCTCGCCGCCGATGATGAAGCGAACCATCTTGTTTATGAAAAAACGGATGGCAA
TGAAACGGTCATGATCATCATCAACCGGAGCAACGAAGCAGCAGAATTCCCATGCCGATCGATGCGCGTGGAAAATGGCTG
GTCAACCTTCTGACAGGGGAGCGGTTCGCTGCAGAGGCGGAAACACTTTGCGTCTCCTTGCCGCCGTACGGGTTTGTGCTTTA
CGCGGTCGAAAGCTGGTA

SEQ ID NO: 61
TATGCCGTCGCCGTACGATGAAACACCTTCGCAAACTGCGTATACCGCTCCACTTGGCGGCGGTCGACGTCATAGCCGATGCC
GGGAGCGTCCGGCACGCGGATCAAGCCGCCGTGCACCTCAACTTCCGGCGTGATGATATCCCGCTCCCAATAATGCGACGAC
GCGGCGGTGTCGCCGGGAAGGGTGAAGTTTTCCAACGTCGTGATCGCGATGTTGTGGGCGCGCCCGACGCCTGCTTCCAGCAT
CCCCCCGCACCAGACCGGCGCACCGCGCTCAGCGCAAAGATCGTGGATGCGCTTCGCCTCGCCAAGCCCGCCAACGCGCCCG
ATTTTGATGTTGATGATGCGACAGCTGCCAAGGTCAAGCGCCTTGCGCGCATCGTCATAGGAACGAATGCTTTCATCAAGGCA
AATCGGCGTCTGAAGAAGCGGCTGCAGCCGAGCGTGATCGACAAGATCGTCAGCGGCGAGCGGCTGCTCGATCATCAGCAAC

TABLE 5-continued

Target gene sequences for *Geobacillus stearothermophilus* (Process Control)

*Geobacillus stearothermophilus* Target Gene Sequences for Process Control

CCGAATTCATCGAGCGCTTTCAGCCGATCCGCATCGACAAGCGTATACGCCGAATTGGCATCGGCCATAAGCGGCACGTCAG
GAAACACGCGCCGCACCTCACGAATGACGTCCACATCCCAGCTTGGCTTGATTTTCACCTTGATCCGCCGGTACCCTTGCGCC
ACATACCGCTCAATCACCTGAAGCAGATCGGCAACCGTCGGCTGGATGCCGATGCTGACGCCGACTTCAATGTCCTTTTTCGC
TCCTCCGAGAGCTTGAGAAAGCGGAACGCCGAGCCGCTTGGCGTACAAATCCCATACCGCCCCCTCAAGCGCCGCTTTCGCC
ATGTTGTTTTGGCGGATGGCAGAAAAGCGCTTTGACAGCTCCTCCGGGTGGTGAATCGGCTCAGCCAACGCAAGCGGCACAA
GGAAATCTTCGAGCATATGCCAGTTCGTTTTCACCGTTTCCTCGCTGTACCACGGGGCGGAAAATGCGACCGATTCGCCCCAG
CCGGAAACGCCGTCGCGATCGACAACTTCCACTAAAATCAACTCTTTCCTTTGAAACGTGCCGAAGCTCGTCGTAAACGGCGC
CTTCAACTCCATTTGTAAATGGCGCAATATGACGTACTCGAT

SEQ ID NO: 62
CGCATGTATGAGCGCATGGCTGCCATTTTTTTCAATGTCGTGCGGATGTGCGCCGTATCGCCCGCCGTCAGCAAATTCGCCAA
ATATTCGATCGGAATGCGCATTTCATCAATGGCCGGGAAGATGTCATCGGCGCTCGCTTGGCTTCCTTTTCCTTCGATCGTATT
CATGATCGGGCTCAGCGGCGGAATGTACCATACCATTGGCAGCGTCCGGTATTCCGGATGCAGCGGCAAAGCGATTTTCCAG
TCGACGATCATTTTGTAAATCGGCGAGCGCTGTGCGGCGGCGATCCATTCGTCTGGGATGCCCGCTTCTTTCGCGGCGGCGGC
GACGGCTGGATCGTTTGGATCAAGGAAAATATCAAGCTGGGCGTGGTACAGCTGTTTCTCATCTGTGACGCTCGCCGCTTCTT
TCACTTTGTCAGCGTCATACAGCATCACACCGATGTAACGGATGCGGCCGACGCACGTTTCCGAACAAATCGTCGGCATGCCG
GCTTCGATGCGCGGGAAGCAGAGCGTGCATTTTTCCGCTTTGTTCGTTTGCCAGTTGAAATACACTTTTTTGTACGGGCAGCTT
GTGACGCAATACCGCCAAGCGCGGCAGGCGTTTTGGTCGACGAGGACGATGCGTCCTCGTCGCGTTTGTACATGGCGCCTG
ACGGGCAGCTCGATACGCATGACGGATTGAGGCAATGCTCGCAAATGCGCGGCAAGTACATCATAAAGACATTCTCAAATTC
CGTTTGGATCGCTTGCTCCATTTTGACAACGTTCGGATCACGCAAACCGGTGATATGGACGCCGGCCAGATCGTCTTCCCAGT
TCGGCCCCCATGACAGCTCCATCCATTCGCCGGTGATGCTTGATTTCGGCCGCGCCACTGGCTGGTATTGTTTTAGCGGGCTGT
TCGTCAACGTTTCATAGTCGTAATTCCACGGTTCGTAGTAATCGTCGATCGTAGGTTGGTACGGATTGTAGAACAAGTTGACG
AGCCGCATCGCTTTCGAGCCGGATTTGAGCCGCAGTTCGCCGTTTTTCAACTCCCAGCCGCCTCTATACTTCTCTTGGTTTTCC
CATTGTTTCGGATAGCCGATTCCGGGTTTCGTTTCAACGTTGTTAAAGTACATGTATTCAGCGCCGGGGCGGTTCGTCCATGTG
TTTTTGCACGTGACGCTGCACGTATGGCAGCCGATGCATTTGTCCAAATTCATCACCATGCCGACTTGCGCTTTAATCTTCAA

SEQ ID NO: 63
ATGCTGTCATTACGTCCTTATGAATTTTGGTTTGTGACAGGAAGTCAGCACTTGTACGGAGAAGAAGCGTTAAAACAAGTCGA
AGAACATTCAAGAATCATGGTCAATGAATGGAATCGCGATTCGGTGTTTCCGTTCCCATTCGTTTTCAAATCAGTCGTGACGA
CGCCAGAGGAAATCCGGCGCGTTTGCCTTGAGGCGAATGCGAGCGAACAATGCGCTGGGGTCATCACTTGGATGCATACATT
CTCGCCAGCGAAAATGTGGATTGGCGGCCTTTTGGAGTTGAGAAAACCGTTATTGCATCTTCACACCCAGTTTAACCGTGATA
TTCCGTGGGACAGCATCGATATGGACTTTATGAACTTAAACCAATCGGCTCACGGTGACCGGGAATACGGATTTATCGGCGCG
AGAATGGGCGTGGCCCGGAAAGTGGTGGTCGGGCACTGGGAAGACCCAGAAGTCCGCGAGCGGCTGGCGAAATGGATGCGG
ACGGCTGTCGCGTTTGCGGAAAGCCGCAACCTAAAAGTGGCTCGTTTTGGCGACAACATGCGTGAAGTGGCTGTGACGGAAG
GGGACAAAGTCGGAGCGCAAATTCAATTCGGCTGGTCGGTCAACGGCTATGGCATCGGGGATTTGGTGCAATACATCCGCGA
TGTTTCTGAACAAAAAGTGAACGAGTTGCTCGATGAATACGAGGAGCTGTACGACATTGTACCCGCCGGCCGCCAAGAAGGG
CCCGTTCGCGAATCAATTCGTGAACAGGCGCGGATTGAACTCGGGCTGAAAGCCTTTTTGCAAGACGGGAACTTCACTGCCTT
TACGACGACGTTTGAAGATTTGCACGGCATGAAGCAACTTCCAGGACTAGCGGTTCAACGGCTTATGGCAGAGGGATATGGA
TTTGGCGGCGAAGGCGACTGGAAAACGGCTGCTCTCGTTCGGTTGATGAAAGTCATGGCGGATGGCAAAGGAACATCGTTCA
TGGAAGACTACACGTACCACTTTGAGCTGGGCAACGAACTGATTCTTGGCGCGCACATATGCTCGAAGTATGCCCGACGATTGCC
GCAACCCGGCCGCGCATCGAAGTCCATCCGCTTTCGATCGGTGGAAAAGAAGATCCAGCCCGTCTCGTGTTTGACGGCGGCG
AGGGTGCTGCGGTCAATGCTTCGTTGATTGACTTAGGACACCGTTTCCGTCTCATTGTCAATGAAGTCGATGCAGTGAAACCA
GAACATGAGATGCCGAAACTGCCTGTTGCGCGCATTCTATGGAAACGCGCCCGTCACTCCGCGACTCGGCCGAAGCATGGA
TTTTAGCCGGCGGAGCGCATCACACATGCTTCTCGTTTGCGGTCACGGCTGAACAGCTGCAAGACTTTGCGGAAATGGCGGGC
ATTGAATGCGTCGTGATCAATGAACATACGTCCGTCTCCTCATTCAAGAACGAACTAAGATGGAATGAAGTATTCTGGCGGG
GGCGGTAAGA

SEQ ID NO: 64
AAATATTCGATCGGAATGCGCATTTCATCAATGGCCGGGAAGATGTCATCGGCGCTCGCTTGGCTTCCTTTTCCTTCGATCGTA
TTCATGATCGGGCTCAGCGGCGGAATGTACCATACCATTGGCAGCGTCCGGTATTCCGGATGCAGCGGCAAAGCGATTTTCCA
GTCGACGATCATTTTGTAAATCGGCGAGCGCTGTGCGGCGGCGATCCATTCGTCTGGGATGCCCGCTTCTTTCGCGGCGGCGG
CGACGGCTGGATCGTTTGGATCAAGGAAAATATCAAGCTGGGCGTGGTACAGCTGTTTCTCATCTGTGACGCTCGCCGCTTCT
TTCACTTTGTCAGCGTCATACAGCATCACACCGATGTAACGGATGCGGCCGACGCACGTTTCCGAACAAATCGTCGGCATGCC
GGCTTCGATGCGCGGGAAGCAGAGCGTGCATTTTTCCGCTTTGTTCGTTTGCCAGTTGAAATACACTTTTTTGTACGGGCAGCT
TGTGACGCAATACCGCCAAGCGCGGCAGGCGTTTTGGTCGACGAGGACGATGCCGTCCTCGTCGCGTTTGTACATGGCGCCTG
ACGGGCAGCTCGATACGCATGACGGATTGAGGCAATGCTCGCAAATGCGCGGCAAGTACATCATAAAGACATTCTCAAATTC
CGTTTGGATCGCTTGCTCCATTTTGACAACGTTCGGATCACGCAAACCGGTGATATGGACGCCGGCCAGATCGTCTTCCCAGT
TCGGCCCCCATGACAGCTCCATCCATTCGCCGGTGATGCTTGATTTCGGCCGCGCCACTGGCTGGTATTGTTTTAGCGGGCTGT
TCGTCAACGTTTCATAGTCGTAATTCCACGGTTCGTAGTAATCGTCGATCGTAGGTTGGTACGGATTGTAGAACAAGTTGACG
AGCCGCATCGCTTTCGAGCCGGATTTGAGCCGCAGTTCGCCGTTTTTCAACTCCCAGCCGCCTCTATACTTCTCTTGGTTTTCC
CATTGTTTCGGATAGCCGATTCCGGGTTTCGTTTCAACGTTGTTAAAGTACATGTATTCAGCGCCGGGGCGGTTCGTCCATG

A PCR primer set for amplifying GBS sequences comprises at least one of the following sets of primer sequences: (1) SEQ ID NOS: 1 and 3; (2) SEQ ID NOS: 4 and 6; (3) SEQ ID NOS: 4 and 7; (4) SEQ ID NOS: 8 and 10; (5) SEQ ID NOS: 11 and 13; (6) SEQ ID NOS: 14 and 16; (7) SEQ ID NOS: 14 and 18; (8) SEQ ID NOS: 19 and 21; (9) SEQ ID NOS: 22 and 24; (10) SEQ ID NOS: 25 and 27; (11) SEQ ID NOS: 22 and 29; (12) SEQ ID NOS: 30 and 32; and (13) SEQ ID NOS: 33 and 35

A probe for binding to a GBS sequence comprises at least one of the following probe sequences: SEQ ID NOS: 2, 5, 9, 12, 15, 17, 20, 23, 26, 28, 31 and 34.

A PCR primer set for amplifying a GBS neuA gene comprises SEQ ID NOS: 1 and 3.

A probe for binding to a GBS neuA gene comprises SEQ ID NO: 2.

A PCR primer set for amplifying a GBS cspA gene comprises at least one of the following sets of primer sequences: (1) SEQ ID NOS: 4 and 6; (2) SEQ ID NO: 4 and 7; and (3) SEQ ID NOS: 8 and 10.

A probe for binding to a GBS cspA gene comprises at least one of the following probe sequences: SEQ ID NOS: 5 and 9.

A PCR primer set for amplifying a GBS cylE gene comprises SEQ ID NOS: 11 and 13.

A probe for binding to a GBS cylE gene comprises SEQ ID NO: 12.

A PCR primer set for amplifying a GBS hylB gene comprises at least one of the following sets of primer sequences: (1) SEQ ID NOS: 14 and 16; and (2) SEQ ID NO:14 and 18.

A probe for binding to a GBS hylB gene comprises at least one of the following probe sequences: SEQ ID NOS: 15 and 17.

A PCR primer set for amplifying a GBS mreA gene comprises SEQ ID NOS: 19 and 21.

A probe for binding to a GBS mreA gene comprises SEQ ID NO: 20.

A PCR primer set for amplifying a GBS ptsI gene comprises at least one of the following sets of primer sequences: (1) SEQ ID NOS: 22 and 24; (2) SEQ ID NO: 25 and 27; (3) SEQ ID NOS: 22 and 29; (4) SEQ ID NOS: 30 and 32; and (5) SEQ ID NOS: 33 and 35

A probe for binding to a GBS ptsI gene comprises at least one of the following probe sequences: SEQ ID NOS: 23, 26, 28, 31 and 34.

Any set of primers can be used simultaneously in a multiplex reaction with one or more other primer sets, so that multiple amplicons are amplified simultaneously.

Example 5

Testing neuA Primer and Probe Sequences for the Ability to Amplify their Intended Target Sequence Certain oligonucleotide sequences listed in Table 2 were tested for their ability to amplify their intended target sequence. As a representative example, an oligonucleotide solution comprising SEQ ID NOS: 1, 2 and 3 was used to amplify the neuA gene of *S. agalactiae* (ATCC No. BAA-1176). In the same polymerase chain reaction (PCR), a plasmid containing a fragment of SEQ ID: 62 (and 64 also contains this sequence) was input as a process control template (*Geobacillus* plasmid). An oligonucleotide solution comprising SEQ ID NOS: 46, 47 and 51 was used to amplify the *Geobacillus* process control. In an additional PCR, water was included as the template control (negative control).

Triplicate reactions where *S. agalactiae* and a *Geobacillus* plasmid were input as templates yielded Ct values indicative of the formation of PCR product, while no Ct values (UND) were obtained in the negative control reaction, thus indicating that the neuA primers and probe amplify and specifically detect the neuA gene of *S. agalactiae* and the *Geobacillus* primers and probe amplify and specifically detect the *Geobacillus* process control.

An amplification plot corresponding to Ct values listed in Table 6 is shown in FIG. 1.

TABLE 6

Ct values showing presence of the neuA gene and process control.

| Replicate | GBS | IC | NEG |
|---|---|---|---|
| 1 | 23.70 | 26.57 | UND |
| 2 | 23.89 | 26.68 | UND |
| 3 | 23.71 | 26.61 | UND |

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims. The contents of all references cited herein are incorporated by reference in their entireties.

What is claimed is:

1. An oligonucleotide set comprising a forward primer consisting of SEQ ID NO: 1; a reverse primer consisting of SEQ ID NO: 3; and a probe comprising a nucleotide sequence and a detectable label, wherein the nucleotide sequence consists of SEQ ID NO: 2.

2. A probe comprising a nucleotide sequence and a detectable label, wherein the nucleotide sequence consists of SEQ ID NO: 2.

3. The probe of claim 2, wherein the-detectable label is selected from the group consisting of: a fluorescent label, a chemiluminescent label, a quencher, a radioactive label, biotin, mass tags and gold.

4. A kit for detecting a Group B Streptococcus sequence in a sample, comprising a probe comprising a nucleotide sequence and a detectable label, wherein the nucleotide sequence consists of SEQ ID NO: 2.

5. The kit of claim 4, further comprising:
(a) a forward primer consisting of SEQ ID NO: 1; and
(b) reverse primer consisting of SEQ ID NO: 3.

6. The kit of claim 4, further comprising a positive control, a process control, a negative control, or a combination thereof.

7. The kit of claim 6, wherein the positive control consists of SEQ ID NO: 36.

8. The kit of claim 4, further comprising at least one reagent selected from the group consisting of detecting reagents, quantitating reagents, monitoring reagents, screening reagents, and Group B Streptococcus sequencing reagents, or a combination thereof.

9. The kit of claim 6, wherein the process control is detectable by a forward primer consisting of SEQ ID NO: 46, and a reverse primer consisting of SEQ ID NO: 51, and wherein the process control target sequence is detectable by a probe consisting of SEQ ID NO: 47 labeled with a detectable label.

10. The oligonucleotide set of claim 1, wherein the detectable label is selected from the group consisting of: a fluorescent label, a chemiluminescent label, a quencher, a radioactive label, biotin, mass tags and gold.

11. An oligonucleotide set comprising at least one forward primer consisting of SEQ ID NO: 1; at least one reverse primer consisting of SEQ ID NO: 3; at least one probe comprising a nucleotide sequence and a detectable label, wherein the nucleotide sequence consists of SEQ ID NO: 2 ; at least one positive control consisting of a Group B Streptococcus plasmid; and at least one negative control comprising purified genomic DNA from *Bacteroides thetaiotaomicron*.

12. The oligonucleotide set of claim 11, wherein the detectable label is selected from the group consisting of: a fluorescent label, a chemiluminescent label, a quencher, a radioactive label, biotin, mass tags and gold.

* * * * *

SEQUENCE LISTING

<160> NUMBER OF SEQ ID NOS: 67

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tcctttgcca tttgataagc atatg                    25

<210> SEQ ID NO 2
<211> LENGTH: 26
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 2
aggttatcgt cgccaagatt tacaac                                         26

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgctatagat atggtgggag cagat                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actgccttaa tgactacaag ttcag                                          25

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cctatctact caacagacgg tactagtcc                                      29

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tagacttata gcttcccaag gcttt                                          25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tatagcttcc caaggctttc aattg                                          25

<210> SEQ ID NO 8
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 8
tctaagccac aacaaatggt gtttg                                            25

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tgttagtgta ggagcttgtc tatccaaagt gatat                                 35

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgtctatct ttgtcataag ttgct                                            25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtagtcacc tccctaagat attga                                            25

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
cctaatttct gtctcctctt ccaaggg                                          27

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atatttcttc atcagagact ttggt                                            25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ttactactgc tactaaagct gaagg                                         25

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
catctatcag aacattacca taggcgc                                       27

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgataggcag caattgtgtc aaac                                          24

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
agaacattac cataggcgcc agt                                           23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcaattgtgt caaaccatct atc                                           23

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcgtcttaac gtttaatgag acacc                                         25

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 20
tcgtctaacc ttcgctcgct tccaacc                                        27

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
taactcatcg acgccatact cttga                                          25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccatacaatc catcaatcct tcgtt                                          25

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
ttgatcaccg gccatctcac cacacat                                        27

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cataccaaca agaagtggaa ccg                                            23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctgaaggtaa atgggcaggt atg                                            23

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 26
tgagatggcc ggtgatcaaa ctgcg                                          25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
taagctacgt gtacgaagta ctgag                                          25

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
cgcagtttga tcaccggcca tctc                                           24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aatcccatac caacaagaag tgga                                           24

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agcaagtttc atacctctat caacc                                          25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
ccggccatct caccacacat acctg                                          25

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
gaagtggaac cgcagtttga tc                                              22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcagaagaag ctcgccttga                                                 20

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
tgcactccaa gcttcacaag acgagc                                          26

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcaaatacag ctgcggcttc ttc                                             23

<210> SEQ ID NO 36
<211> LENGTH: 159
<212> TYPE: DNA
<213> ORGANISM: Streptococcus sp.

<400> SEQUENCE: 36
tcctttgcca tttgataagc atatgtccta gaggtgaaaa agctttttc ccttaagtaa      60 gtttctttat tagaaataaa aatagcgccg ttcggatagt ataaaggttg taaatcttgg    120
cgacgataac ctttatctgc tcccaccata tctatagca                           159

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttttcatttg ctcaaaatca acc                                             23

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
```

```
gagccgatca ctgtccgtcc gg                                              22

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agttgcagcg cattatttta aaagg                                           25

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtggaaacga tccggaatgc                                                 20

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
aaatgtatgg tgtgggatac agagaag                                         27

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgatcagttg cttgacatgt tcat                                            24

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcaacttccg gcgtgatga                                                  19

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
```

```
tatcccgctc ccaataatgc gacgacg                                        27
```

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

```
gatcacgacg ttggaaaact tcac                                           24
```

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
tcggaatgcg catttcatca atg                                            23
```

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47

```
ccgggaagat gtcatcggcg c                                              21
```

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

```
tgagcccgat catgaatacg atc                                            23
```

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

```
ctcgccgatt tacaaaatga t                                              21
```

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

```
tcgccgattt acaaaatgat cgtc                                           24
```

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggcatcccag acgaatgg                                                 18

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cagcgctcgc cgatt                                                    15

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcgaatgcga gcgaacaa                                                 18

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
ctccaaaagg ccgccaatcc acat                                          24

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gtgtgaagat gcaataacgg ttttc                                         25

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
tattcgatcg gaatgcgcat ttca                                          24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
caagcgagcg ccgatgacat cttc                                            24

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
cgatcatgaa tacgatcgaa ggaaa                                           25

<210> SEQ ID NO 59
<211> LENGTH: 3562
<212> TYPE: DNA
<213> ORGANISM: Geobacillus stearothermophilus

<400> SEQUENCE: 59
tttttaggaa accggcttgt gccaagatca atgttttttt atttggacaa ctccatgagc      60
aaatcgcctg cctggatcgc atcgccgctt ttgacgtaaa tgtctttgac aacaccggca     120
aacggtgctt gcacggtcgt ttccattttc attgcttccg tgaccattaa atggtcccct     180
ttgtcgactt ttttccccttt ttcgacaagc actttaacaa ccgtacccgg catcgtcgcc    240
gcaatatggt tcgggttcgt ccgatccgct ttaatgtgct caacgactgc ggttttaatg     300 cttttcatcgc ggatgacaac ttcacgcggt tgaccgttca gctcgaagta gacgacgcgt    360
gtaccgtccg cctgcggctg gccgatcgac acaagcttaa cgatcaacgt ttttccgcgc     420
tcgatttcca cttcaatttc ctcgccaagg cgcatgccat acaagaacgt cggtgtatcg     480
agtacagaca catcgccgta ttttccacc gtttctgcat attcaagaaa cactttcgga     540
taaagggcgt acgcaatggc atcaaagtcg gtcacttcgc ggccaagctt gtcatacagc     600 tctttttttca tttgctcaaa atcaaccggc tcgagcagtt cccccggacg gacagtgatc    660
ggctcgcgtc cttttaaaat aatgcgctgc aactctttcg ggaatccgcc gtgcggctgg    720
cctaaatatc cttcaaacag ctcgacgact gaatcaggga agttcagcgt ttcgccgcgc    780
tcgaaaatgt cttgttccgt caagttgttt tgcaccatgt aaagcgccat atcgccgacg    840
actttcgatg acggcgtcac tttgacaata tcgccgaaca agtcgttgac gcggcggtac    900
atttctttca cttcatccca ccgatcgccg agaccgaccg cttttcgcctg ctgctgcaag   960 ttgctgtatt gaccgcctgg catttcgtgc atgtacactt ccgtatgcgg cgcgttcatg   1020
ccgctttcaa attcttgata aaacttgcgc acatcttccc aatagcgcgc taactgctca   1080
agaccgtaaa tgtcgacttc cggcgcccgc tcggtcccctt caagcgcata gtaaagcgta   1140
ttggcgctcg gctgagacgt taagccggcc atcgaactga tggcgacatc aacaatatca   1200
acgccggctt caatcgctttt cgcgtacgta taaatgccgt taccgctcgt gtcgtgcgta   1260
tgcaaataaa tcggaatgtc gactgttcc ttgagcccgg aaatgagcac atgcgccgcc    1320
tgcggcttca agagccccgc catatcttta atggccaaaa tgtgcgcacc cgcctgttca   1380

```
agctctttcg caagggcctt atagtaatcc aaattgtatt tcgaccggct cggatctaaa   1440
atatcacccg tatagcaaat cgccgcttca gcgattttgc cgctctgccg gacggcgtcg   1500
atcgccaccg tcattccttt cacccagttt aaactgtcga aaattcggaa cacatggatg   1560
ccagcatgcg ccgattttc gacgaactcg cggatgacgt tgtccggata gttttgtag   1620
cctacggcgt tggcagaacg gagcaacatt tggaacaaca cgttcgggaa tgcgtcgcgc   1680
agcttcagaa gccgatccca cggatcctct tttaaaaagc gatacgccac atcaaacgtc   1740
gccccgcccc acatttcaag cgagaataaa ttcggcaata agcgcgcgct cggctcggct   1800
gcacgcacta atcgaccgt gcggactcgt gtcgccaaca gtgactgatg agcgtcccgg   1860
aacgtcgtat cggtcaagag cacccgcggc tgttcttgaa tccagcggac aagcccctcg   1920
gggccatgct tgtccaaaat ttgcttcgtt ccggccggga tcggtctgc ctcgctcaat   1980
tttggcaagc gcggcttgtc aaacaccggc ttttctttt tgccgatgcc tgggaatcca   2040
ttgaccgtca ctgtgccgat gtaagtgagc attttcgttc gcggtctttt ccggcgtggg   2100
aacacgaata gttccggcgt cgtatcgatg aacgacgtat cgtattcgcc tgataaaaac   2160
ttcggatgtt ggacgacatt ttccaagaac ggaatgttcg ttttaaatac gcgaatgcgg   2220
aacgtccgca agttgcgcag cattttcctt gctgcctgct caaacgtcaa cgcccatgtc   2280
gacaatttga cgagcaagga atcgtaatac ggcgtaatga ctgccccttg gaaaccgttg   2340
ccggcgtcca aacgtacacc aaagcccca ccggagcgat acgccattat tttcccagta   2400
tctggcataa agttattgag cgggtcttcc gtcgtcaccc gcgactgaat ggcataaccg   2460
ttaatgcgga tgtcttcctg cttcggaatg ccgacttcat ggctatgaag cgaacagcca   2520
tcagcaatta aaatttgcga ctggacgata tcaattccag taatcatctc ggtgatcgta   2580
tgctcgactt gaatgcgcgg gttgacttcg atgaaataaa actcatcacc cgaaacgaga   2640
aattcgaccg tgccggcatt gacataaccg acgcttctca taagctgaac cgctgcctcg   2700
caaatgcgtt ggcgcagctc gtccgacagc gagacgctcg gcgcgacttc gacgactttt   2760
tggtggcggc gctgcaccga gcagtcgcgt tcataaaggt gaacgatatt tccttcatag   2820
tcacctaaaa tttgcacttc aatgtgcttt ggattttcga tcaacttttc aacatacacc   2880
tcatcgctgc caaacgccgc ttttgcttcc gatttggcac gctcaaacgc ttctttaact   2940
tccgacttcg aacggacgaa tcgcatgccg cgcccaccgc cgccaagtgc tgctttaatg   3000
atgatcggat agccgtgcgc ttcggcgaaa gcgacaacgt cctcaaggcc gtcgaccggc   3060
ccgtcgctgc ccggaatgac cggaatgcca gcgttcaccg ccgcatggcg cgctttcacc   3120
ttgtcgccga acatgtccaa atggttctca ttcgggccaa aaaaataat tccttcttca   3180
cggcaccgtt tagcaaattg aatatttct gaaaaaaacc catatcctgg gtgaatcgca   3240
tcgacatcgt gggccttggc aatctcaatg atgccttcaa tatccaaata cgcctcaatc   3300
ggcttttttc cttcaccgac taaatacgct tcatccgctt tatagcggtg gtatgagccg   3360
acatcttcct tcgagtaaat ggccacggtg cggatgccaa gctccgtgca ggcgcggaaa   3420
acgcggatgg cgatctcccc gcggttagct acgagcactt tgcgaattcg tcttgtcttc   3480
atcgtctttc ctccttttcta atttaaacta taaaactttt tctattttgt aaatacactt   3540
tctaaaaagt cagacctctt tt                                            3562
```

<210> SEQ ID NO 60
<211> LENGTH: 1755
<212> TYPE: DNA

<213> ORGANISM: Geobacillus stearothermophilus

<400> SEQUENCE: 60

```
agccatccac caccgctcaa ccgaccattt cgcttatgct tatgacagcg agacgctcca      60
tctccggctt caaacaaaga aacatgatgt cgaccacgtc gagctgcttt ttggcgaccc     120
gtacgaatgg cacgatggcg cctggcagtt tcaaacgatg ccgatgcgga aaacgggaag     180
cgacggttg tttgactatt ggctcgccga agtcaaaccg ccatatcgac ggctgcgcta     240
tgggtttgtg cttcgagctg gggacgagaa actggtctat acggaaaaag gattttacca     300
tgaagctccg agcgacgaca ccgcttacta cttttgcttc ccctttcttc atcgggtcga     360
cctattccaa gcgccggact gggtaaaaga cacagtatgg tatcaaattt tccccgagcg     420
gttcgccaac ggcaacccgg ccatcagtcc gaaaggggcg cggccgtggg aagcgagga     480
cccgacgccg acgagctttt cggcggcga cttgcaagga atcatcgatc accttgacta     540
tttggctgat ctcggcatca ccggcattta cttgacgccg attttccgcg cgccgtcgaa     600
tcataaatac gacaccgctg attatttga aatcgacccg cactttgggg acaaagagac     660
gttgaaaaca cttgtcaagc gctgccatga aaaagggatc cgcgtcatgc tcgatgcagt     720
cttcaatcat tgcggctatg agtttgcccc gtttcaagat gtgttaaaaa acggtgcagc     780
gtctaggtat aaagattggt tccatattcg cgagtttccg ctccaaacgg agccgcgccc     840
gaattacgac acatttgcgt tcgtgccgca atgcccaaa ctcaatacccg cccatccgga     900
agtgaagcgc tacttgcttg atgtcgcgac gtactggatt cgcgagtttg atattgacgg     960
ctggcggctc gatgtggcaa acgaaatcga tcaccaattt tggcgcgaat ccgtcaggc    1020
ggtgaaggcg ctaaagcccg atgtgtacat tctcggcgag atttggcatg atgccatgcc    1080
gtggctgcg gcgaccaat ttgacgccgt catgaactac ccgttcacgg acggagcgct    1140
tcgcttttc gcgaaagagg aaatcagcgc ccgccagttt gccgatatca tggtccggtt    1200
gcttcattcg tatccgaaac atgtgaacga agcggcgttt aacttgcttg cagccatga    1260
tacaccaagg ctgctcactg tttgcggcgg cgacgtccgc aaagcgaagt tgttgttttt    1320
gttccagctc acgttcactg gttcgccgtg tatttactat ggcgatgaga tcggcatgac    1380
gggtggaaac gatccggaat gccggaaatg tatggtgtgg gatacagaga agcaaaacaa    1440
agaactgtat gaacatgtca agcaactgat cgctcttcgc aggcaatatc gggcgcttcg    1500
acgcggcgat gtcgcttttc tcgccgccga tgatgaagcg aaccatcttg tttatgaaaa    1560
aacggatggc aatgaaacgg tcatgatcat catcaaccgg agcaacgaag cagcagaaat    1620
tcccatgccg atcgatgcgc gtggaaaatg gctggtcaac cttctgacag gggagcggtt    1680
cgctgcagag gcgaaacac tttgcgtctc cttgccgccg tacgggtttg tgctttacgc    1740
ggtcgaaagc tggta                                                    1755
```

<210> SEQ ID NO 61
<211> LENGTH: 1115
<212> TYPE: DNA
<213> ORGANISM: Geobacillus stearothermophilus

<400> SEQUENCE: 61

```
tatgccgtcg ccgtacgatg aaacaccttc gcaaactgcg tataccgctc cacttggcgg      60
cggtcgacgt catagccgat gccgggagcg tccggcacgc ggatcaagcc gccgtgcacc     120
tcaacttccg gcgtgatgat atcccgctcc caataatgcg acgacgcggc ggtgtcgccg     180
ggaagggtga agtttccaa cgtcgtgatc gcgatgttgt gggcgcgccc gacgcctgct     240
```

-continued

```
tccagcatcc ccccgcacca gaccggcgca ccgcgctcag cgcaaagatc gtggatgcgc      300
ttcgcctcgc caagcccgcc aacgcgcccg attttgatgt tgatgatgcg acagctgcca      360
aggtcaagcg ccttgcgcgc atcgtcatag gaacgaatgc tttcatcaag gcaaatcggc      420
gtctgaagaa gcggctgcag ccgagcgtga tcgacaagat cgtcagcggc gagcggctgc      480
tcgatcatca gcaacccgaa ttcatcgagc gctttcagcc gatccgcatc gacaagcgta      540
tacgccgaat tggcatcggc cataagcggc acgtcaggaa acacgcgccg cacctcacga      600
atgacgtcca catcccagct tggcttgatt ttcaccttga tccgccggta cccttgcgcc      660
acataccgct caatcacctg aagcagatcg gcaaccgtcg gctggatgcc gatgctgacg      720
ccgacttcaa tgtcctttt cgctcctccg agagcttgag aaagcggaac gccgagccgc       780
ttggcgtaca aatcccatac cgccccctca agcgccgctt cgccatgtt gttttggcgg       840 atggcagaaa agcgctttga cagctcctcc gggtggtgaa tcggctcagc caacgcaagc      900
ggcacaagga aatcttcgag catatgccag ttcgttttca ccgtttcctc gctgtaccac      960
ggggcggaaa atgcgaccga ttcgccccag ccggaaacgc cgtcgcgatc gacaacttcc     1020
actaaaatca actctttcct ttgaaacgtg ccgaagctcg tcgtaaacgg cgccttcaac     1080
tccatttgta aatggcgcaa tatgacgtac tcgat                                1115

<210> SEQ ID NO 62
<211> LENGTH: 1247
<212> TYPE: DNA
<213> ORGANISM: Geobacillus stearothermophilus

<400> SEQUENCE: 62
cgcatgtatg agcgcatggc tgccattttt ttcaatgtcg tgcggatgtg cgccgtatcg       60
cccgccgtca gcaaattcgc caaatattcg atcggaatgc gcatttcatc aatggccggg      120
aagatgtcat cggcgctcgc ttggcttcct tttccttcga tcgtattcat gatcgggctc      180
agcggcggaa tgtaccatac cattggcagc gtccggtatt ccggatgcag cggcaaagcg      240 atttttccagt cgacgatcat tttgtaaatc ggcgagcgct gtgcggcggc gatccattcg      300
tctgggatgc ccgcttcttt cgcggcggcg gcgacggctg gatcgtttgg atcaaggaaa      360
atatcaagct gggcgtggta cagctgtttc tcatctgtga cgctcgccgc ttctttcact      420
ttgtcagcgt catacagcat cacaccgatg taacggatgc ggccgacgca cgtttccgaa      480
caaatcgtcg gcatgccggc ttcgatgcgc gggaagcaga gcgtgcattt ttccgctttg      540
ttcgtttgcc agttgaaata cacttttttg tacgggcagc ttgtgacgca ataccgccaa      600
gcgcggcagg cgttttggtc gacgaggacg atgccgtcct cgtcgcgttt gtacatggcg      660
cctgacgggc agctcgatac gcatgacgga ttgaggcaat gctcgcaaat gcgcggcaag      720
tacatcataa agacattctc aaattccgtt tggatcgctt gctccattt gacaacgttc       780 ggatcacgca aaccggtgat atggacgccg gccagatcgt cttcccagtt cggccccat       840 gacagctcca tccattcgcc ggtgatgctt gatttcggcc gcgccactgg ctggtattgt      900
tttagcgggc tgttcgtcaa cgtttcatag tcgtaattcc acggttcgta gtaatcgtcg      960
atcgtaggtt ggtacggatt gtagaacaag ttgacgagcc gcatcgcttt cgagccggat     1020
ttgagccgca gttcgccgtt tttcaactcc cagccgcctc tatacttctc ttggttttcc     1080
cattgtttcg gatagccgat tccgggtttc gtttcaacgt tgttaaagta catgtattca     1140
gcgccggggc ggttcgtcca tgtgttttg cacgtgacgc tgcacgtatg gcagccgatg      1200
```
catttgtcca aattcatcac catgccgact tgcgctttaa tcttcaa 1247

<210> SEQ ID NO 63
<211> LENGTH: 1493
<212> TYPE: DNA
<213> ORGANISM: Geobacillus stearothermophilus

<400> SEQUENCE: 63

| | | |
|---|---|---|
| atgctgtcat tacgtcctta tgaattttgg tttgtgacag gaagtcagca cttgtacgga | 60 |
| gaagaagcgt taaaacaagt cgaagaacat tcaagaatca tggtcaatga atggaatcgc | 120 |
| gattcggtgt ttccgttccc attcgttttc aaatcagtcg tgacgacgcc agaggaaatc | 180 |
| cggcgcgttt gccttgaggc gaatgcgagc gaacaatgcg ctggggtcat cacttggatg | 240 |
| catacattct cgccagcgaa aatgtggatt ggcggccttt tggagttgag aaaaccgtta | 300 |
| ttgcatcttc acacccagtt taaccgtgat attccgtggg acagcatcga tatggacttt | 360 |
| atgaacttaa accaatcggc tcacggtgac cgggaatacg gatttatcgg cgcgagaatg | 420 |
| ggcgtggccc ggaaagtggt ggtcgggcac tgggaagacc cagaagtccg cgagcggctg | 480 |
| gcgaaatgga tgcggacggc tgtcgcgttt gcggaaagcc gcaacctaaa agtggctcgt | 540 |
| tttggcgaca acatgcgtga agtggctgtg acggaagggg acaaagtcgg agcgcaaatt | 600 |
| caattcggct ggtcggtcaa cggctatggc atcggggatt tggtgcaata catccgcgat | 660 |
| gtttctgaac aaaaagtgaa cgagttgctc gatgaatacg aggagctgta cgacattgta | 720 |
| cccgccggcc gccaagaagg gcccgttcgc gaatcaattc gtgaacaggc gcggattgaa | 780 |
| ctcgggctga aagccttttt gcaagacggg aacttcactg cctttacgac gacgtttgaa | 840 |
| gatttgcacg gcatgaagca acttccagga ctagcggttc aacggcttat ggcagaggga | 900 |
| tatggatttg gcggcgaagg cgactggaaa acggctgctc tcgttcggtt gatgaaagtc | 960 |
| atggcggatg gcaaaggaac atcgttcatg gaagactaca cgtaccactt tgagctgggc | 1020 |
| aacgaactga ttcttggcgc gcatatgctc gaagtatgcc cgacgattgc cgcaaccccgg | 1080 |
| ccgcgcatcg aagtccatcc gctttcgatc ggtggaaaag aagatccagc ccgtctcgtg | 1140 |
| tttgacggcg gcgagggtgc tgcggtcaat gcttcgttga ttgacttagg acaccgtttc | 1200 |
| cgtctcattg tcaatgaagt cgatgcagtg aaaccagaac atgagatgcc gaaactgcct | 1260 |
| gttgcgcgca ttctatggaa accgcgcccg tcactccgcg actcggccga agcatggatt | 1320 |
| ttagccggcg gagcgcatca cacatgcttc tcgtttgcgg tcacggctga acagctgcaa | 1380 |
| gactttgcgg aaatgcggg cattgaatgc gtcgtgatca atgaacatac gtccgtctcc | 1440 |
| tcattcaaga acgaactaag atggaatgaa gtattctggc ggggggcggta aga | 1493 |

<210> SEQ ID NO 64
<211> LENGTH: 1081
<212> TYPE: DNA
<213> ORGANISM: Geobacillus stearothermophilus

<400> SEQUENCE: 64

| | | |
|---|---|---|
| aaatattcga tcggaatgcg catttcatca atggccggga agatgtcatc ggcgctcgct | 60 |
| tggcttcctt ttccttcgat cgtattcatg atcgggctca gcggcggaat gtaccatacc | 120 |
| attggcagcg tccggtattc cggatgcagc ggcaaagcga ttttccagtc gacgatcatt | 180 |
| ttgtaaatcg gcgagcgctg tgcggcggcg atccattcgt ctgggatgcc cgcttctttc | 240 |
| gcggcggcgc cgacgctggg atcgtttgga tcaaggaaaa tatcaagctg ggcgtggtac | 300 |
| agctgttcct catctgtgac gctcgccgct tctttcactt tgtcagcgtc atacagcatc | 360 |

```
acaccgatgt aacggatgcg gccgacgcac gtttccgaac aaatcgtcgg catgccggct      420
tcgatgcgcg ggaagcagag cgtgcatttt tccgctttgt tcgtttgcca gttgaaatac      480
acttttttgt acgggcagct tgtgacgcaa taccgccaag cgcggcaggc gttttggtcg      540
acgaggacga tgccgtcctc gtcgcgtttg tacatggcgc ctgacgggca gctcgatacg      600
catgacggat tgaggcaatg ctcgcaaatg cgcggcaagt acatcataaa gacattctca      660
aattccgttt ggatcgcttg ctccattttg acaacgttcg gatcacgcaa accggtgata      720
tggacgccgg ccagatcgtc ttcccagttc ggcccccatg acagctccat ccattcgccg      780
gtgatgcttg atttcggccg cgccactggc tggtattgtt ttagcgggct gttcgtcaac      840
gtttcatagt cgtaattcca cggttcgtag taatcgtcga tcgtaggttg gtacggattg      900
tagaacaagt tgacgagccg catcgctttc gagccggatt tgagccgcag ttcgccgttt      960
ttcaactccc agccgcctct atacttctct tggttttccc attgtttcgg atagccgatt     1020
ccgggtttcg tttcaacgtt gttaaagtac atgtattcag cgccggggcg gttcgtccat     1080
g                                                                     1081
```

<210> SEQ ID NO 65
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
aaacacgtgc                                                               10

<210> SEQ ID NO 66
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
ccttgttcca                                                               10

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
cagggacgat                                                               10